(12) United States Patent
Lahaye et al.

(10) Patent No.: US 9,133,467 B2
(45) Date of Patent: Sep. 15, 2015

(54) PATHOGEN-INDUCIBLE PROMOTERS AND THEIR USE IN ENHANCING THE DISEASE RESISTANCE OF PLANTS

(75) Inventors: Thomas Lahaye, Halle (DE); Patrick Römer, Riesdorf (DE); Sebastian Schornack, Norwich (GB); Jens Boch, Halle (DE); Ulla Bonas, Halle (DE)

(73) Assignee: Two Blades Foundation, Evanston, IL (US)

( * ) Notice: Subject to any disclaimer, the term of this patent is extended or adjusted under 35 U.S.C. 154(b) by 937 days.

(21) Appl. No.: 12/615,506

(22) Filed: Nov. 10, 2009

(65) Prior Publication Data

US 2010/0132069 A1   May 27, 2010
US 2013/0219555 A9   Aug. 22, 2013

Related U.S. Application Data

(60) Provisional application No. 61/113,206, filed on Nov. 10, 2008.

(51) Int. Cl.
*C12N 15/82* (2006.01)
*C12N 15/10* (2006.01)
*C12Q 1/68* (2006.01)

(52) U.S. Cl.
CPC ........ *C12N 15/8239* (2013.01); *C12N 15/1072* (2013.01); *C12N 15/8281* (2013.01); *C12Q 1/6897* (2013.01)

(58) Field of Classification Search
None
See application file for complete search history.

(56) References Cited

FOREIGN PATENT DOCUMENTS

WO    WO 2009/042753 A1    4/2009

OTHER PUBLICATIONS

Boch, Jens et al., "Breaking the Code of DNA Binding Specificity of TAL-Type III Effectors," *Science*, 2009, vol. 326, pp. 1509-1512.

Jordan, Tina et al., "Physical delimitation of the pepper Bs3 resistance gene specifying recognition of the AvrBs3 protein from *Xanthomonas campestris* pv. vesicatoria," *Theor Appl Genet*, 2006, vol. 113, pp. 895-905.

Kay, Sabine et al., "A Bacterial Effector Acts as a Plant Transcription Factor and Induces a Cell Size Regulator," *Science*, 2007, vol. 318, pp. 648-651.

Kay, Sabine et al., "Detailed analysis of the Dna recognition motifs of the Xanthomonas type III effectors AvrBs3 and AvrBs3Δrep16," *The Plant Journal*, 2009, vol. 59, pp. 859-871.

Marois, Eric et al., "*The Xanthomonas* Type III Effector Protein AvrBs3 Modulates Plant Gene Expression and Induces Cell Hypertrophy in the Susceptible Host," *MPMI*, 2002, vol. 15(7), pp. 637-646.

Römer, Patrick et al., "Plant Pathogen Recognition Mediated by Promoter Activation of the Pepper Bs3 Resistance Gene," *Science*, 2007, vol. 318, pp. 645-648.

Römer, Patrick et al., "A single plant resistance gene promoter engineered to recognize multiple Tal effectors from disparate pathogens," *PNAS*, 2009, vol. 106(48), pp. 20526-20531 (including supporting online material).

Römer, Patrick et al., "Recognition of AvrBs3-Like Proteins Is Mediated by Specific Binding to Promoters of Matching Pepper Bs3 Alleles[1 FF]"*Plant Physiology*, 2009, vol. 150, pp. 1697-1712.

Hummel, Aaron W. et al., "Addition of transcription activator-like effector binding sites to a pathogen strain-specific rice bacterial blight resistance gene makes it effective against additional strains and against bacteral leaf streak", *New Phytologist*, 2012, pp. 1-11.

*Primary Examiner* — Elizabeth McElwain
(74) *Attorney, Agent, or Firm* — Williams Mullen PC; David M. Saravitz

(57) ABSTRACT

Methods for producing pathogen-inducible promoters for the expression of genes in plants are provided. The pathogen-inducible promoters are inducible by one, two, three, or more plant pathogens. Methods for producing R genes that are inducible in a plant by more than one plant pathogen are further provided. Additionally, provided are R genes and other nucleic acid molecules comprising the pathogen-inducible promoters and that are made by such methods as well as plants, plant parts, plant cells, seeds, and non-human host cells comprising the R genes and other nucleic acid molecules.

67 Claims, 4 Drawing Sheets

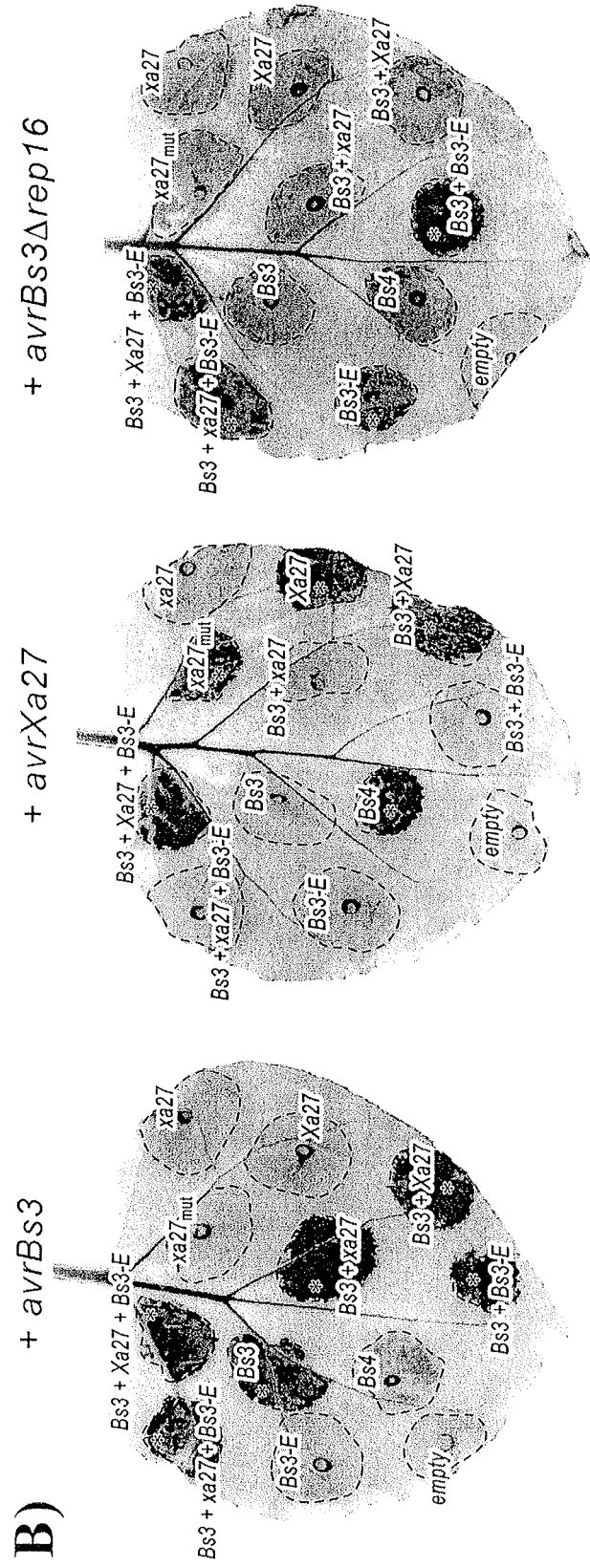

SEQUENCE LISTING

```
<160> NUMBER OF SEQ ID NOS: 48

<210> SEQ ID NO 1
<211> LENGTH: 2244
<212> TYPE: DNA
<213> ORGANISM: Capsicum annuum
<220> FEATURE:
<221> NAME/KEY: gene
<222> LOCATION: (0)...(0)
<223> OTHER INFORMATION: Bs3

<400> SEQUENCE: 1
atgatgaatc agaattgctt taattcttgt tcacctctaa ctgttgatgc acttgaacca      60
aaaaaatcct cttgtgctgc taaatgcata caagtaaatg gtcctcttat tgttggagct     120
ggcccttcag gcctggctac tgctgccgtc cttaagcaat acagtgttcc gtatgtaatc     180
attgaacgcg cggactgcat tgcttctctg tggcaacaca agacctacga tcggcttagg     240
cttaacgtgc cacgacaata ctgcgaattg cctggcttgc catttccacc agactttcca     300
gagtatccaa ccaaaaacca attcatcagc tacctcgtat cttatgcaaa gcatttcgag     360
atcaaaccac aactcaacga gtcagtaaac ttagctggat atgatgagac atgtggttta     420
tggaaggtga aaacagtttc tgaaatcaat ggttcaacct ctgaatacat gtgtaagtgg     480
cttattgtgg ccacaggaga gaatgctgag atgatagtgc ccgaattcga aggattgcaa     540
gattttggtg gccaggttat tcatgcttgt gagtacaaga ctggggaata ctatactgga     600
gaaaatgtgc tggcggttgg ctgtggcaat tccgggatcg atatctcact tgatctttcc     660
caacataatg caaatccatt catggtagtt cgaagctcgg taagttttat attcaataag     720
tattattttt caagtaacac tagaaagtga tcttgtatct ttcatttgct cgcatgaata     780
tattatattc acacatgaat gatatcatct agttttgtta atctttcagg tacagggtcg     840
taatttccct gaggaaataa acatagttcc agcaatcaag aaatttactc aaggaaaagt     900
agaatttgtt aatggacaaa ttctagagat cgactctgtt atcttggcaa ctggttatac     960
cagcaatgta acttcttggt taatggtaag gaaatacaca agttttattt ctatgcctaa    1020
ttaaattggt gtttaatcat aaattatata tagtactaag tatgataaaa gctccttcaa    1080
ctataaagga tgatttagtc aaatgaactc ttaatgaatg tagtaattat ttatggattc    1140
ttgttacatt catgtaagtt ggtatctcat tatcctgtgg attctttcct ttgagttatt    1200
aattagttag aattcactat aaccgtcttt tttcttttac cctttcctca taccttttg     1260 ttcttttgat aactcgaact cacaatctta agattgggaa taagggctc tttaccatct     1320 gagcaacttt ctctcgttct ataatagccc ccttcgaaat ttggtctaat gagaattta     1380 ctgatacagg agagtgaatt gttttcaagg gagggatgtc caaaaagccc attcccaaat    1440
ggttggaagg gggaggatgg tctctatgca gttggattta caggaatagg actgtttggt    1500
```

-continued

```
gcttctatag atgccactaa tgttgcacaa gatattgcca aaatttggaa agaacaaatg    1560
tagcacaaga atcataatca atctgttgga tgcatgccat ggagaagaag caagttactt    1620
ttctcatgtc aagaaaataa gatttttttt tttcttcctg taatattact gggattggat    1680
attctcccag ttgccttttg tttgatttgt gtcatgtgtg aaaataataa tttaatggtt    1740
tgtaagttat tcttctattt gatgttttaa gtcacttgtt ttatattttt cctgtgatgg    1800
atttatatta tgaatttta tataaattat ttttttttcc ttttcaagg ttgcatttca    1860 ataccagtca tattaaccat tttcgaactc tacttctttt tatgacatag attttgaagc    1920 attttctgt gaccccactc acaattagga ttcatttggt acaaacaact agcccgtggc    1980
gagtcaacta tgagggcata tatatatata tttttttttc catttagact tgaactatcc    2040
tactttatgg tattaatcga gccatgtttc aacttagaat tttcattcat attattagag    2100
gctttctaga ttgaatttgt taaattttat gggtctaatt ccacactta ttatgactag    2160 gcttatgagg atatgctagg ggtcttcttg accttcattg gtctgagatg tccgttacgg    2220
tcaggacctg cactcagatc atga                                            2244
```

<210> SEQ ID NO 2
<211> LENGTH: 4499
<212> TYPE: DNA
<213> ORGANISM: Lycopersicon esculentum
<220> FEATURE:
<221> NAME/KEY: gene
<222> LOCATION: (0)...(0)
<223> OTHER INFORMATION: Bs4

<400> SEQUENCE: 2

```
atggcatctt cttcttcttc ttctgcaagt aattcaaagt attatcctcg atggaagtac      60
gttgtttttc taagtttcag aggtgaagac actcgaaaaa catttacagg tcacttatac     120
gaaggtttga gaatagagg aataaacaca tttcaagatg ataaaagact agagcatgga     180
gattcaattc caaagaact cttgagagct atagaagatt ctcaagttgc acttatcatt     240
ttctcaaaga attatgctac atctaggtgg tgcttgaatg aactagtgaa gatcatggaa     300
tgcaaagagg aagaaaatgg acaaacagtc ataccgatct tttataatgt ggatccatca     360
catgttcgat accaaactga aagctttgga gcagcatttg ccaaacacga atcaaagtat     420
aaggatgatg ttgaggggat gcagaaggtg caaagatgga gaactgccct aactgctgcc     480
gcaaatctaa aaggatatga tatccgtaac gggttagttg aatacacata attactttta     540
atgtttttac tgttaaaaag gcatagtcca atcaatttaa ttagagaaga tacataaaag     600
tccaaaaaac tattcaagtt ttgcaacttc catacttgaa actatagag tattgttatt     660 acctgaacta ttctatttcc tatttaatac cctgctgatt attaacaata tatatagagt     720
atatgaaata cttgttggta tttgactttc ttacattgtc cacaatcaat tttcttcttt     780
atgtaggatt gaatcagaga atattcagca gatcgtagat tgcatctctt ccaaatttg     840 tacgaatgct tattctttat cttttttgca agatattgtg ggaataaatg ctcacttaga     900
gaaactaaaa tcgaaacttc aaatagaaat caatgatgtt cggatttag ggatctgggg     960 aataggcgga gtcggtaaaa caagaatagc aaaagccatt tttgatactc tatcttatca    1020
atttgaagct tcttgttttc ttgctgatgt taaagaattt gcaaaaaaga ataaactgca    1080 ttcttttacaa atattcttc tctctgaact gttaaggaaa aaaatgatt acgtctacaa    1140 caagtatgat ggaaagtgta tgattccaaa cagactttgt tctttgaagg ttctaattgt    1200
```

```
gcttgatgat atagatcatg gtgatcagat ggagtattta gcaggtgata tttgttggtt    1260
tggtaatggc agcagagtta ttgtaacaac tagaaacaaa catttgatag agaaagatga    1320
tgcgatatac gaagtgtcta cactgcctga tcatgaagct atgcaattat tcaatatgca    1380
tgcttttaaa aaagaagttc caaatgagga ttttaaggag ttggcgttag agatagtaaa    1440
tcacgctaaa ggcctccctt tagccctcaa ggtgtgggc tgtttattgc ataaaaaaaa    1500
tctctcttta tggaaaataa cagtagagca aataaagaaa gactctaatt cagaaattgt    1560
tgaacaactc aaaataagtt atgatgggtt ggagtccgaa gagcaggaaa tattttaga    1620 tatagcatgt ttcttccgcg agagaaaag aaaagaggtc atgcaaattc ttaagagttg    1680
tgactttgga gctgaatacg gattggatgt tctgattaat aaatctcttg tgttcatatc    1740
tgaaaatgac aggattgaaa tgcatgattt gattagagat atgggtagat atgtggtgaa    1800
aatgcaaaag cttcagaaaa aacgtagcag aatatgggat gttgaagatt tcaaagaagt    1860
gatgatagac tatacggtaa gtaagcttaa caatgcaatg atatttaatt tctaatttt    1920 atattccaag gaacttatag gctaatcaat acagtttatg aataattgac tcattgatct    1980
ttataccagg ggaccatgac agtggaagca atctggttta gttgctttga agaagtacgt    2040
tttaataagg aggcaatgaa aaaaatgaaa aggcttagga tattacacat atttgatggt    2100
tttgtcaaat tcttctcttc gcctccctct tccaattcca atgattcaga agaagaagat    2160
gattcctacg acttagtcgt agatcaccat gatgactcta ttgagtacct gtccaataac    2220
ttgcgttggt tagtctggaa tcactattct tggaagtcat tgccagaaaa ttttaaacca    2280
gaaaagcttg ttcatcttga actccgttgg agttcgcttc attatttatg gaagaaaaca    2340
gaggtaacat tattatttac tttacttacc ctcctccagg agcttcaacc cctttttgctc    2400 tcttatttac tcgaacccac aaccttttgg gttggaagtg agggtgctca actccctctt    2460 gtcattttg gtctgacaca aagatcatta ttctttctct attttgaata acagcatttg    2520
ccgtctctac gaaagctaga tctcagctta tctaaaagtc tggtgcaaac accagatttc    2580
acggggatgc caaatttgga gtatttgaat ctggagtact gtagtaagct tgaagaggtt    2640
cactattccc tagcatattg cgaaaaactc attgagttaa atttgagttg gtgtacaaag    2700
cttaggagat ttccatatat taacatggaa tctcttgaat ctctggatct acaatattgc    2760
tatggtataa tggtgttttcc agaaatcatc ggaacgatga agccggagtt aatgattctc    2820
tcagcaaaca ctatgataac tgaactacca tcatctcttc agtacccaac tcatctcaca    2880
gagctagatt tgagtggcat ggaaaaacctt gaagctcttc caagcagcat tgtcaagttg    2940
aaagatttgg tgaagctaaa tgtgtcgtac tgcttaacgc ttaaaagctt gcctgaagag    3000
attggtgatt tagaaaactt ggaggaactt gatgcttcgc gtactctaat ttcacagcct    3060
ccatcttcca ttgtccgctt gaacaagctt aaatccttga agttaatgaa acgaaacaca    3120
ttaacagatg atgtgtgctt tgtgtttcct cctgtgaata acgggttact ctcattggaa    3180
attctggagc tcggttcctc caatttcgaa gatggaagaa ttccggaaga tattggatgt    3240
ttatcctctt tgaaagagtt acgtctcgag ggagataatt tcaatcattt gcctcaaagc    3300
atagcccaac ttggtgcact tcgattctta tacataaaag attgcaggag tcttacaagt    3360
ctgccagaat ttccaccgca attagataca atatttgcag attggagcaa tgatttgatc    3420
tgtaagtcac tgtttctaaa tatctcatca ttccaacata acatctctgc ttcagattcg    3480
ttgtcgttaa gagtgtttac gagtttgggg agtagtatcc caatctggtt ccaccatcag    3540
ggaacagata caagtgtttc agtcaatttg cctgaaaact ggtatgtatc agataacttc    3600
```

```
ttgggattcg ctgtatgtta ctatggcaat ttaactgaga acacagctga attgattatg    3660
agttctgcag ggatgccatg tatcacctgg aaacttttgt tatcgaatca ttcagaatgt    3720
acatatatta ggattcattt tttcttggta ccttttgctg cttatggga tacatctaac     3780 gccaatggta aaacaccaaa tgactataag cacattatgt tatcttttcc tcaagaattg    3840
aaggagtgtg gagttcgttt gttctatgaa gatgaatctg tgcttgagac caccaatgat    3900
gaacttacca ttggggtaag gaggatcaga tacgacgacg acgatagtga acattatgag    3960
gaggctggtt gttcctcttc taagaaacaa agatcataat ataggtatat aaacttgtga    4020
tcacttgctg tttgttatta ataattcatt tcgatgctct atgtggttgt taaatatctc    4080
tcatgttatg acagggagca gaggcggagc cagaattttc aataagaggg ctcaaaatct    4140
gtagaaatag atagctgaag gggtttgaca tcttactata tatatacata taaacttatt    4200
ttaaccatgt ataaataata taattttttcg tcgaatgggg tttggatgaa cccttctat    4260 gaaggtacaa tgaagcatca atcaaagtgt gagacagtgg aggaacgttc acatatagca    4320
aacataaaaa tcatatttgt atgttatagt tatagttagc atcattgtaa attttgtaca    4380
aatgtttcag ttctttatta attcatttg tacattgtaa atttgtataa taacatctgt    4440
atttgtataa ttataagtgt atatgatgaa tatatatgta tatatatact tttctctcg    4499
```

<210> SEQ ID NO 3
<211> LENGTH: 1024
<212> TYPE: DNA
<213> ORGANISM: Capsicum annuum
<220> FEATURE:
<221> NAME/KEY: gene
<222> LOCATION: (0)...(0)
<223> OTHER INFORMATION: Bs3
<220> FEATURE:
<221> NAME/KEY: promoter
<222> LOCATION: (1)...(1024)
<220> FEATURE:
<221> NAME/KEY: misc_feature
<222> LOCATION: (905)...(922)
<223> OTHER INFORMATION: upa-AvrBs3 box

<400> SEQUENCE: 3

```
ctacggaata gcagcattaa ggcacatcag agattttttg ggtgttaagt ttgtcatgaa      60
acctgatgcc tccacaggaa ctgtcaatct catgtgtctt ggctctggtt ttcagaattt     120
atccagaaaa gtatcatgat aaattaatgg tgtctgtgtt tggtggctta gagtgacggc     180
tagatcaaca tctttgggat gccttgtgga gtgaaatcaa gcatacttta tcataggcga     240 aatttttttgt tgtggtttgc tgcttgtaat gagagagtga tataggaagc aaatgtggag    300
atcacatttg ctcatctcct tgttgcgttg aaacttttgg tgtcaagagt tctaattcac    360
atgtatttga agattcctca tatgctgctt ttgtttctaa ttattttttc tagtaagaaa    420
acatttgttc ctgagtttcc aactagaaaa aaatatcaag taaaatagaa ttcaatcatt    480
tcccttacca acgcttggta ctgccaaccg caacaaagaa ttaatgcaaa acaacagtct    540
attaatatca acctagacta aactccttag ttttactttg aaatgcgaat gatacatgac    600
acattagatt gtacttgctt tttaccacag atacaacgat acatttgtat atcttttccc    660
ttatagcaaa ctctaatata tcatagtcaa gctaacgaaa cttatgcaag ggaaatatga    720
aattagtatg caagtaaact caaagaacta atcattgaac tgaaagatca atatatcaaa    780
aaaaaaaaaa aaacaataaa accgtttaac cgatagatta accatttctg gttcagttta    840
tgggttaaac cacaatttgc acaccctggt taaacaatga acacgtttgc ctgaccaatt    900
```

```
ttattatata aacctaacca tcctcacaac ttcaagttat catccccttt ctcttttctc      960
ctcttgttct tgtcacccgc taaatctatc aaaacacaag tagtcctagt tgcacatata     1020
tttc                                                                  1024

<210> SEQ ID NO 4
<211> LENGTH: 1037
<212> TYPE: DNA
<213> ORGANISM: Capisucum annuum
<220> FEATURE:
<221> NAME/KEY: gene
<222> LOCATION: (0)...(0)
<223> OTHER INFORMATION: Bs3-E
<220> FEATURE:
<221> NAME/KEY: promoter
<222> LOCATION: (1)...(1037)
<220> FEATURE:
<221> NAME/KEY: misc_feature
<222> LOCATION: (899)...(943)
<223> OTHER INFORMATION: upa-AvrBs3deltarep16 box

<400> SEQUENCE: 4
ctacggaata gcagcattaa ggcacatcag agattttttg ggtgttaagt ttgtcatgaa       60
acctgatgcc tccacaggaa ctgtcaatct catgtgtctt ggctctggtt ttcagaattt      120
atccagaaaa gtatcatgat aaattaatgg tgtctgtgtt tggtggctta gagtgacggc      180
tagatcaaca tctttgggat gccttgtgga gtgaaatcaa gcatacttta tcataggcga      240
aattttttgt tgtggtttgc tgcttgtaat gagagagtga tataggaagc aaatgtggag      300
atcacatttg ctcatctcct tgttgcgttg aaacttttgg tgtcaagagt tctaattcac      360
atgtatttga agattcctca tatgctgctt ttgtttctaa ttattttttc tagtaagaaa      420
acatttgttc ctgagtttcc aactagaaaa aaatatcaag taaaatagaa ttcaatcatt      480
tcccttacca acgcttggta ctgccaaccg caacaaagaa ttaatgcaaa acaacagtct      540
attaatatca acctagacta aactccttag ttttactttg aaatgcgaat gatacatgac      600
acattagatt gtacttgctt tttaccacag atacaacgat acatttgtat atcttttccc      660
ttatagcaaa ctctaatata tcatagtcaa gctaacgaaa cttatgcaag ggaaatatga      720
aattagtatg caagtaaact caaagaacta atcattgaac tgaaagatca atatatcaaa      780
aaaaaaaaaa aaacaataaa accgtttaac cgatagatta accatttctg gttcagttta      840
tgggttaaac cacaatttgc acaccctggt taaacaatga acacgtttgc ctgaccaatt      900
ttattatata aacctctcta ttccactaaa ccatcctcac aacttcaagt tatcatcccc      960
tttctctttt ctcctcttgt tcttgtcacc cgctaaatct atcaaaacac aagtagtcct     1020
agttgcacat atatttc                                                    1037

<210> SEQ ID NO 5
<211> LENGTH: 1024
<212> TYPE: DNA
<213> ORGANISM: Capsicum annuum
<220> FEATURE:
<221> NAME/KEY: gene
<222> LOCATION: (0)...(0)
<223> OTHER INFORMATION: Bs3 upa-mut
<220> FEATURE:
<221> NAME/KEY: promoter
<222> LOCATION: (1)...(1024)
<220> FEATURE:
<221> NAME/KEY: misc_feature
<222> LOCATION: (905)...(922)
<223> OTHER INFORMATION: upa-mut box
<220> FEATURE:
```

<221> NAME/KEY: misc_difference
<222> LOCATION: 905
<223> OTHER INFORMATION: A at position 905 is a T in Bs3 UPA Box

<400> SEQUENCE: 5

```
ctacggaata gcagcattaa ggcacatcag agatttttg ggtgttaagt ttgtcatgaa      60
acctgatgcc tccacaggaa ctgtcaatct catgtgtctt ggctctggtt ttcagaattt     120
atccagaaaa gtatcatgat aaattaatgg tgtctgtgtt tggtggctta gagtgacggc     180
tagatcaaca tctttgggat gccttgtgga gtgaaatcaa gcatacttta tcataggcga    240
aattttttgt tgtggtttgc tgcttgtaat gagagagtga tataggaagc aaatgtggag    300
atcacatttg ctcatctcct tgttgcgttg aaacttttgg tgtcaagagt tctaattcac    360
atgtatttga agattcctca tatgctgctt ttgtttctaa ttatttttc tagtaagaaa    420
acatttgttc ctgagtttcc aactagaaaa aaatatcaag taaaatagaa ttcaatcatt    480
tcccttacca acgcttggta ctgccaaccg caacaaagaa ttaatgcaaa acaacagtct    540
attaatatca acctagacta aactccttag ttttactttg aaatgcgaat gatacatgac    600
acattagatt gtacttgctt tttaccacag atacaacgat acatttgtat atcttttccc    660
ttatagcaaa ctctaatata tcatagtcaa gctaacgaaa cttatgcaag ggaaatatga    720
aattagtatg caagtaaact caaagaacta atcattgaac tgaaagatca atatatcaaa    780
aaaaaaaaa aaacaataaa accgtttaac cgatagatta accatttctg gttcagttta    840
tgggttaaac cacaatttgc acccctggt taaacaatga acacgtttgc ctgaccaatt    900
ttataatata aacctaacca tcctcacaac ttcaagttat catccccttt ctcttttctc    960
ctcttgttct tgtcacccgc taaatctatc aaaacacaag tagtcctagt tgcacatata   1020
tttc                                                                1024
```

<210> SEQ ID NO 6
<211> LENGTH: 1059
<212> TYPE: DNA
<213> ORGANISM: Artificial Sequence
<220> FEATURE:
<221> NAME/KEY: gene
<222> LOCATION: (0)...(0)
<223> OTHER INFORMATION: Bs3 upa294
<220> FEATURE:
<221> NAME/KEY: promoter
<222> LOCATION: (1)...(1059)
<220> FEATURE:
<221> NAME/KEY: misc_feature
<222> LOCATION: (731)...(765)
<223> OTHER INFORMATION: insertion comprising upa-AvrBs3 box
<220> FEATURE:
<221> NAME/KEY: misc_feature
<222> LOCATION: (940)...(957)
<223> OTHER INFORMATION: Bs3 upa-mut box
<220> FEATURE:
<221> NAME/KEY: misc_difference
<222> LOCATION: 940
<223> OTHER INFORMATION: A at position 940 is a T in Bs3 upa box
<223> OTHER INFORMATION: Synthetic Promoter

<400> SEQUENCE: 6

```
ctacggaata gcagcattaa ggcacatcag agatttttg ggtgttaagt ttgtcatgaa      60
acctgatgcc tccacaggaa ctgtcaatct catgtgtctt ggctctggtt ttcagaattt     120
atccagaaaa gtatcatgat aaattaatgg tgtctgtgtt tggtggctta gagtgacggc     180
tagatcaaca tctttgggat gccttgtgga gtgaaatcaa gcatacttta tcataggcga    240
aattttttgt tgtggtttgc tgcttgtaat gagagagtga tataggaagc aaatgtggag    300
```

| | |
|---|---|
| atcacatttg ctcatctcct tgttgcgttg aaacttttgg tgtcaagagt tctaattcac | 360 |
| atgtatttga agattcctca tatgctgctt ttgtttctaa ttattttttc tagtaagaaa | 420 |
| acatttgttc ctgagtttcc aactagaaaa aaatatcaag taaaatagaa ttcaatcatt | 480 |
| tcccttacca acgcttggta ctgccaaccg caacaaagaa ttaatgcaaa acaacagtct | 540 |
| attaatatca acctagacta aactccttag ttttactttg aaatgcgaat gatacatgac | 600 |
| acattagatt gtacttgctt tttaccacag atacaacgat acatttgtat atcttttccc | 660 |
| ttatagcaaa ctctaatata tcatagtcaa gctaacgaaa cttatgcaag ggaaatatga | 720 |
| aattagtatg caattttatt atataaacct aaccatcctc acaaccaagt aaactcaaag | 780 |
| aactaatcat tgaactgaaa gatcaatata tcaaaaaaaa aaaaaaaaca ataaaaccgt | 840 |
| ttaaccgata gattaaccat ttctggttca gtttatgggt taaaccacaa tttgcacacc | 900 |
| ctggttaaac aatgaacacg tttgcctgac caattttata atataaacct aaccatcctc | 960 |
| acaacttcaa gttatcatcc cctttctctt ttctcctctt gttcttgtca cccgctaaat | 1020 |
| ctatcaaaac acaagtagtc ctagttgcac atatatttc | 1059 |

<210> SEQ ID NO 7
<211> LENGTH: 1059
<212> TYPE: DNA
<213> ORGANISM: Artificial Sequence
<220> FEATURE:
<223> OTHER INFORMATION: Synthetic promoter
<220> FEATURE:
<221> NAME/KEY: gene
<222> LOCATION: (1)...(1059)
<223> OTHER INFORMATION: Bs3 upa424
<220> FEATURE:
<221> NAME/KEY: promoter
<222> LOCATION: (1)...(1059)
<220> FEATURE:
<221> NAME/KEY: misc_feature
<222> LOCATION: (600)...(634)
<223> OTHER INFORMATION: insertion comprising upa-AvrBs3 box
<220> FEATURE:
<221> NAME/KEY: misc_feature
<222> LOCATION: (940)...(957)
<223> OTHER INFORMATION: Bs3 upa-mut upa box
<220> FEATURE:
<221> NAME/KEY: misc_difference
<222> LOCATION: 940
<223> OTHER INFORMATION: A at position 940 is a T in Bs3 UPA Box

<400> SEQUENCE: 7

| | |
|---|---|
| ctacggaata gcagcattaa ggcacatcag agatttttg ggtgttaagt ttgtcatgaa | 60 |
| acctgatgcc tccacaggaa ctgtcaatct catgtgtctt ggctctggtt ttcagaattt | 120 |
| atccagaaaa gtatcatgat aaattaatgg tgtctgtgtt tggtggctta gagtgacggc | 180 |
| tagatcaaca tctttgggat gccttgtgga gtgaaatcaa gcatacttta tcataggcga | 240 |
| aattttttgt tgtggtttgc tgcttgtaat gagagagtga tataggaagc aaatgtggag | 300 |
| atcacatttg ctcatctcct tgttgcgttg aaacttttgg tgtcaagagt tctaattcac | 360 |
| atgtatttga agattcctca tatgctgctt ttgtttctaa ttattttttc tagtaagaaa | 420 |
| acatttgttc ctgagtttcc aactagaaaa aaatatcaag taaaatagaa ttcaatcatt | 480 |
| tcccttacca acgcttggta ctgccaaccg caacaaagaa ttaatgcaaa acaacagtct | 540 |
| attaatatca acctagacta aactccttag ttttactttg aaatgcgaat gatacatgac | 600 |
| aattttatta tataaaccta accatcctca caaccacatt agattgtact tgctttttac | 660 |
| cacagataca acgatacatt tgtatatctt ttcccttata gcaaactcta atatatcata | 720 |

```
gtcaagctaa cgaaacttat gcaagggaaa tatgaaatta gtatgcaagt aaactcaaag    780
aactaatcat tgaactgaaa gatcaatata tcaaaaaaaa aaaaaaaaca ataaaaccgt    840
ttaaccgata gattaaccat ttctggttca gtttatgggt taaaccacaa tttgcacacc    900
ctggttaaac aatgaacacg tttgcctgac caatttttata atataaacct aaccatcctc    960
acaacttcaa gttatcatcc cctttctctt ttctcctctt gttcttgtca cccgctaaat   1020
ctatcaaaac acaagtagtc ctagttgcac atatatttc                          1059

<210> SEQ ID NO 8
<211> LENGTH: 131
<212> TYPE: DNA
<213> ORGANISM: Lycopersicon esculentum
<220> FEATURE:
<221> NAME/KEY: gene
<222> LOCATION: (0)...(0)
<223> OTHER INFORMATION: Bs4
<220> FEATURE:
<221> NAME/KEY: promoter
<222> LOCATION: (1)...(131)
<220> FEATURE:
<221> NAME/KEY: TATA_signal
<222> LOCATION: (67)...(73)

<400> SEQUENCE: 8
gatcaaagcg aatgttaata caagctttca cgtttcaagt ggtacttgtt taattcttct     60
ttcttgtata taactttgtc caaaatatca tcaattgatc tcatccatac aatttatttt    120
taatcgaatc t                                                         131

<210> SEQ ID NO 9
<211> LENGTH: 166
<212> TYPE: DNA
<213> ORGANISM: Artificial Sequence
<220> FEATURE:
<223> OTHER INFORMATION: Synthetic promoter
<220> FEATURE:
<221> NAME/KEY: gene
<222> LOCATION: (1)...(166)
<223> OTHER INFORMATION: BS4 upa
<220> FEATURE:
<221> NAME/KEY: promoter
<222> LOCATION: (1)...(166)
<220> FEATURE:
<221> NAME/KEY: misc_feature
<222> LOCATION: (32)...(66)
<223> OTHER INFORMATION: insertion sequence comprising upa-AvrBs3 box
<220> FEATURE:
<221> NAME/KEY: TATA_signal
<222> LOCATION: (102)...(108)

<400> SEQUENCE: 9
gatcaaagcg aatgttaata caagctttca ccaattttat tatataaacc taaccatcct     60
cacaacgttt caagtggtac ttgtttaatt cttctttctt gtatataact tgtccaaaa    120 tatcatcaat tgatctcatc catacaattt atttttaatc gaatct                   166

<210> SEQ ID NO 10
<211> LENGTH: 166
<212> TYPE: DNA
<213> ORGANISM: Artificial Sequence
<220> FEATURE:
<223> OTHER INFORMATION: Synthetic promoter
<220> FEATURE:
<221> NAME/KEY: gene
<222> LOCATION: (1)...(166)
<223> OTHER INFORMATION: Bs4 upa-mut
<220> FEATURE:
```

```
<221> NAME/KEY: promoter
<222> LOCATION: (1)...(166)
<220> FEATURE:
<221> NAME/KEY: misc_feature
<222> LOCATION: (32)...(66)
<223> OTHER INFORMATION: Insertion comprising upa-mut box
<220> FEATURE:
<221> NAME/KEY: misc_difference
<222> LOCATION: (49)...(50)
<223> OTHER INFORMATION: GG at positions 49-50 is CC in wild-type Bs3
      upa box
<220> FEATURE:
<221> NAME/KEY: misc_difference
<222> LOCATION: (54)...(55)
<223> OTHER INFORMATION: GG at positions 49-50 is CC in wild-type Bs3
      upa box
<220> FEATURE:
<221> NAME/KEY: TATA_signal
<222> LOCATION: (2)...(108)

<400> SEQUENCE: 10
gatcaaagcg aatgttaata caagctttca ccaatttat tatataaagg taaggatcct        60
cacaacgttt caagtggtac ttgtttaatt cttctttctt gtataaact ttgtccaaaa       120 tatcatcaat tgatctcatc catacaattt attttaatc gaatct                      166

<210> SEQ ID NO 11
<211> LENGTH: 1557
<212> TYPE: DNA
<213> ORGANISM: Oryza sativa
<220> FEATURE:
<221> NAME/KEY: gene
<222> LOCATION: (0)...(0)
<223> OTHER INFORMATION: Xa27
<220> FEATURE:
<221> NAME/KEY: promoter
<222> LOCATION: (1)...(1557)
<220> FEATURE:
<221> NAME/KEY: misc_feature
<222> LOCATION: (1461)...(1497)
<223> OTHER INFORMATION: upa-AvrXa27 box
<220> FEATURE:
<221> NAME/KEY: misc_difference
<222> LOCATION: (1476)...(1478)
<223> OTHER INFORMATION: GAA sequence that is absent from xa27 promoter
<220> FEATURE:
<221> NAME/KEY: misc_difference
<222> LOCATION: 1485
<223> OTHER INFORMATION: C at position 1517 is an A in the
      corresponding position of the xa27 promoter

<400> SEQUENCE: 11
ctgcagctga accaaacagt tttagctcca tcgaagaaag gagttatact gattggaatg        60
ctctcacagt aaaaaaaaca aggaagtaga gctggatttt agacagttct acaagaagtt       120
agaactctac caaaattgga attttggatg atggtctttt aaaaactcga ttgcaggaat       180
aaaattttac ggcttgaaac ttacaaaatg attagaaaag ataacatgcc tcagcgattt       240
gtaaaaaagt gaacaaataa aaatctacaa taccactaaa ctattgcttt attttgggga       300
cattgcttac cattgaaaaa acaactaacc gtaaatacga acacccatat caaatatact       360
atcactgata aaataatcaa ttgtaaattc aagcacacat attagtatag tactttaact       420
cgattggata gaagaaacct aactaattta agctatgcct cacaacaaaa aggtatataat      480 tttttaaggc ttcttttttt ttcttgcgtt tgctagttta tgcttttaag atgtttatac       540 ctttactcc cctcattcac tgtttaaata caatgggaat tagtgaaatc aatgagagtt        600
caaacttcga aacactgaat acatgttatt ttggattgaa atcaaatcga atcagtcaaa       660
ttcaaatagg aggaggaaca taggcattct tcctttcttc agcgggcacc attgaattca       720
```

```
gatactgctt cgcctagtct ctgtccaaga ctccacattt tctgatggtg atggggaact      780
ctgaaactat aggaggaaga ataaaatgaa gaatgcagaa atgaatagta atttgtgttt      840
tttaattctt cttcaattcc accttaggat ccaacttcag tccaaatcca agtaatgca      900 actgccacta gatcaggcta gagcttcaaa ttcaactcca aaaacctccg taaagtggca      960
cacacagagg aaaaatcctg gattcgtcac tgcccatcaa catctgcttt cgcctcccaa     1020
ttcctgcttt ctgaaatctg ctttcgccga attcatgcct tcttgaatta tgctttctta     1080
gaccctcttt agatgggact aaaactttta ctctctatca catcggatgt ttggacacta     1140
attataaata ttaaacgtag actattaata aaacccatct ataatcttgt attaattcgc     1200
gagacgaatc tattgagcct aattaatcca tgattagcct atgtgatgct ataataaaca     1260
ttctctaatt ataaattaat tgggcttaaa aaatttgtct cgcgtattag ctttcattta     1320
tataattagt tttataaata gtctatattt aatactctaa attagtgtct aaatacaggg     1380
actaaagtta agtcactgga tccaaacacc acctaaggtt ttcttgtgta cttgtgaatt     1440
gtggttgact acgactacta gtgctataaa tagaagaaga gacccataga gagcatcaga     1500
gcaaagtact cctaaaagac agccacacac actgagacac ccaagaagct gcctcca       1557
```

<210> SEQ ID NO 12
<211> LENGTH: 1589
<212> TYPE: DNA
<213> ORGANISM: Oryza sativa
<220> FEATURE:
<221> NAME/KEY: gene
<222> LOCATION: (0)...(0)
<223> OTHER INFORMATION: xa27
<220> FEATURE:
<221> NAME/KEY: promoter
<222> LOCATION: (1)...(1589)
<220> FEATURE:
<221> NAME/KEY: misc_feature
<222> LOCATION: (1496)...(1529)
<223> OTHER INFORMATION: upa-Avrxa27 box
<220> FEATURE:
<221> NAME/KEY: misc_difference
<222> LOCATION: 1517
<223> OTHER INFORMATION: A at position 1517 is a C in the corresponding
      position of the Xa27 promoter

<400> SEQUENCE: 12

```
ctgcagctga accaaacagt tttagctcca tcgaagaaag gagttatact gattggaatg       60
ctcacagtta aaaaaaacaa ggaagtagag ctggatttta gacagttcta taagaagtta      120
gaactctacc aaacggatag ttaattggaa ttttggatga tggtctttta aaaactcgat      180
tgcaggaata aaattttacg gcttgaaact tacaaaatga ttagaaaaga taacatgcct      240
cagcgatttg taaaaagtg aacaaataaa aatctacaat accactaaac tattgcttta      300
ttttggggac attgcttacc attgaaaaaa caactaaccg taaatacgaa cacccatgtc      360
aaatatacta tcactgataa aataatcaat tgtaaattca agcacacata ttagtatagt      420
actttaactc gattggatag aagaaaccta actaatttaa gctatgcctc acaacaaaaa      480
ggtataaatt tttaaggct tcttttttttt ttcttgcgtt tgctagttta tgcttttaag       540
atgtttatac tttttactcc cctcattcac tgtttaaata caatgggaat tagtgaaatc      600
aatgagagtt caaacttcga aacactgaat acatgttatt ttggattgaa atcaaatcga      660
atcagtcaaa ttcaaatagg aggaggaaca taggcattct tccttctctc agcgggcacc      720
attgaattca gatactgctt cgcctagtct ctgtccaaga ctccacattt tctgatggtg      780
```

-continued

| | |
|---|---|
| atggggaact ctgaaactat aggaggaaga ataaaatgaa gaatgcagaa atgaatagta | 840 |
| atttgtgttt tttaattctt cttcaattcc accttaggat ccaacttcag tccaaatcca | 900 |
| aagtaatgca actgccacta gatcaggcta gagcttcaaa ttcaactcca aaaacctccg | 960 |
| taaagtggca cacacagagg aaaaatcctg gattcgtcac tgcccatcaa catctgcttt | 1020 |
| cgcctcccaa ttcctgcttt ctgaaatctg ctttcgccga attcatgcct tcttgaatta | 1080 |
| tgctttctta gaccctcttt agatgagact aaaactttta ctctctatca catcggatgt | 1140 |
| ttggacacta attataaata ttaaacgtag actattaata aaacccatct ataatcttgt | 1200 |
| attaattcgc gtgacgaatc tattgagcct aattaatcca tgattagcct atgtgatgct | 1260 |
| ataataaaca ttctctaatt ataaattaat tgggcttaaa aaatttgtct cgcgtattag | 1320 |
| ctttcattta tgtaattagt tttataaata gtctatattt aatactctaa attagtgtct | 1380 |
| aaatacaggg actaaagtta agtccctgga tccaaacgcc acctaaggtt ttcttgtgta | 1440 |
| cttgtgaatt gtggtttctt gtgtacttgt gaattgtggt tgactacgac tacgagtgct | 1500 |
| ataaatagaa gagaccaata gagagcatca gagcaaagta ctcctaaaag acagccacac | 1560 |
| acactgagac acccaagaag ctgcctcca | 1589 |

```
<210> SEQ ID NO 13
<211> LENGTH: 1070
<212> TYPE: DNA
<213> ORGANISM: Artificial Sequence
<220> FEATURE:
<223> OTHER INFORMATION: Synthetic promoter
<220> FEATURE:
<221> NAME/KEY: promoter
<222> LOCATION: (1)...(1070)
<223> OTHER INFORMATION: Bs3 and Bs3E
<220> FEATURE:
<221> NAME/KEY: misc_feature
<222> LOCATION: (734)...(781)
<223> OTHER INFORMATION: upa-AvrBs3deltarep16 box
<220> FEATURE:
<221> NAME/KEY: misc_feature
<222> LOCATION: (952)...(969)
<223> OTHER INFORMATION: upa-AvrBs3 box

<400> SEQUENCE: 13
```

| | |
|---|---|
| ctacggaata gcagcattaa ggcacatcag agattttttg ggtgttaagt ttgtcatgaa | 60 |
| acctgatgcc tccacaggaa ctgtcaatct catgtgtctt ggctctggtt ttcagaattt | 120 |
| atccagaaaa gtatcatgat aaattaatgg tgtctgtgtt tggtggctta gagtgacggc | 180 |
| tagatcaaca tctttgggat gccttgtgga gtgaaatcaa gcatacttta tcataggcga | 240 |
| aattttttgt tgtggtttgc tgcttgtaat gagagagtga tataggaagc aaatgtggag | 300 |
| atcacatttg ctcatctcct tgttgcgttg aaacttttgg tgtcaagagt tctaattcac | 360 |
| atgtatttga agattcctca tatgctgctt ttgtttctaa ttatttttc tagtaagaaa | 420 |
| acatttgttc ctgagtttcc aactagaaaa aaatatcaag taaatagaa ttcaatcatt | 480 |
| tcccttacca acgcttggta ctgccaaccg caacaaagaa ttaatgcaaa acaacagtct | 540 |
| attaatatca acctagacta aactccttag ttttactttg aaatgcgaat gatacatgac | 600 |
| acattagatt gtacttgctt tttaccacag atacaacgat acatttgtat atctttttccc | 660 |
| ttatagcaaa ctcaatatat tcatagtcaa gctaacgaaa cttatgcaag ggaaatatga | 720 |
| aattagtatg caattttatt atataaacct ctctattcca ctaaaccatc ctcacaacca | 780 |
| agtaaactca agaactaatt cattgaactg aaagatcaat atatcaaaaa aaaaaaaaa | 840 |
| caataaaacc gtttaaccga tagattaacc atttctggtt cagtttatgg gttaaaccac | 900 |

-continued

```
aatttgcaca ccctggttaa acaatgaaca cgtttgcctg accaatttta ttatataaac    960
ctaaccatcc tcacaacttc aagttatcat ccccttctc ttttctcctc ttgttcttgt   1020
cacccgctaa atctatcaaa acacaagtag tcctagttgc acatatattt             1070

<210> SEQ ID NO 14
<211> LENGTH: 1107
<212> TYPE: DNA
<213> ORGANISM: Artificial Sequence
<220> FEATURE:
<223> OTHER INFORMATION: Synthetic Promoter
<220> FEATURE:
<221> NAME/KEY: promoter
<222> LOCATION: (1)...(1107)
<223> OTHER INFORMATION: Bs3 and Xa27 and Bs3E
<220> FEATURE:
<221> NAME/KEY: misc_feature
<222> LOCATION: (734)...(781)
<223> OTHER INFORMATION: upa-AvrBs3deltarep16 box
<220> FEATURE:
<221> NAME/KEY: misc_feature
<222> LOCATION: (913)...(949)
<223> OTHER INFORMATION: upa-AvrXa27 box
<220> FEATURE:
<221> NAME/KEY: misc_feature
<222> LOCATION: (989)...(1006)
<223> OTHER INFORMATION: upa-AvrBs3 box

<400> SEQUENCE: 14
ctacggaata gcagcattaa ggcacatcag agattttttg ggtgttaagt ttgtcatgaa     60
acctgatgcc tccacaggaa ctgtcaatct catgtgtctt ggctctggtt ttcagaattt    120
atccagaaaa gtatcatgat aaattaatgg tgtctgtgtt tggtggctta gagtgacggc    180
tagatcaaca tctttgggat gccttgtgga gtgaaatcaa gcatacttta tcataggcga    240 aatttttgt tgtggtttgc tgcttgtaat gagagagtga tataggaagc aaatgtggag     300
atcacatttg ctcatctcct tgttgcgttg aaacttttgg tgtcaagagt tctaattcac    360
atgtatttga agattcctca tatgctgctt ttgtttctaa ttattttttc tagtaagaaa    420
acatttgttc ctgagtttcc aactagaaaa aaatatcaag taaaatagaa ttcaatcatt    480
tcccttacca acgcttggta ctgccaaccg caacaaagaa ttaatgcaaa acaacagtct    540
attaatatca acctagacta aactccttag ttttactttg aaatgcgaat gatacatgac    600
acattagatt gtacttgctt tttaccacag atacaacgat acatttgtat atcttttccc    660
ttatagcaaa ctctaatata tcatagtcaa gctaacgaaa cttatgcaag ggaaatatga    720
aattagtatg caatttttatt atataaacct ctctattcca ctaaaccatc ctcacaacca    780
agtaaactca agaactaat cattgaactg aaagatcaat atatcaaaaa aaaaaaaaa    840 caataaaacc gtttaaccga tagattaacc atttctggtt cagtttatgg gttaaaccac    900
aatttgcaca ccgtgctata aatagaagaa gagacccata gagagcatcc tggttaaaca    960
atgaacacgt ttgcctgacc aattttatta taaacctaa accatcctca caacttcaag   1020
ttatcatccc ctttctcttt tctcctcttg ttcttgtcac ccgctaaatc tatcaaaaca   1080
caagtagtcc tagttgcaca tatattt                                     1107

<210> SEQ ID NO 15
<211> LENGTH: 1059
<212> TYPE: DNA
<213> ORGANISM: Artificial Sequence
<220> FEATURE:
<223> OTHER INFORMATION: Synthetic Promoter
<220> FEATURE:
```

<221> NAME/KEY: promoter
<222> LOCATION: (1)...(1059)
<223> OTHER INFORMATION: Bs3 and Xa27
<220> FEATURE:
<221> NAME/KEY: misc_feature
<222> LOCATION: (865)...(901)
<223> OTHER INFORMATION: upa-AvrXa27 box
<220> FEATURE:
<221> NAME/KEY: misc_feature
<222> LOCATION: (941)...(958)
<223> OTHER INFORMATION: upa-AvrBs3 box

<400> SEQUENCE: 15

```
ctacggaata gcagcattaa ggcacatcag agatttttg ggtgttaagt ttgtcatgaa       60
acctgatgcc tccacaggaa ctgtcaatct catgtgtctt ggctctggtt ttcagaattt     120
atccagaaaa gtatcatgat aaattaatgg tgtctgtgtt tggtggctta gagtgacggc     180
tagatcaaca tctttgggat gccttgtgga gtgaaatcaa gcatacttta tcataggcga    240
aattttttgt tgtggtttgc tgcttgtaat gagagagtga tataggaagc aaatgtggag    300
atcacatttg ctcatctcct tgttgcgttg aaacttttgg tgtcaagagt tctaattcac    360
atgtatttga agattcctca tatgctgctt ttgtttctaa ttattttttc tagtaagaaa    420
acatttgttc ctgagtttcc aactagaaaa aaatatcaag taaaatagaa ttcaatcatt    480
tcccttacca acgcttggta ctgccaaccg caacaaagaa ttaatgcaaa acaacagtct    540
attaatatca acctagacta aactccttag ttttactttg aaatgcgaat gatacatgac    600
acattagatt gtacttgctt tttaccacag atacaacgat acatttgtat atcttttccc    660
ttatagcaaa ctctaatata tcatagtcaa gctaacgaaa cttatgcaag ggaaatatga    720
aattagtatg caagtaaact caaagaacta atcattgaac tgaaagatca atatatcaaa    780
aaaaaaaaaa aacaataaaa ccgtttaacc gatagattaa ccatttctgg ttcagttttat    840 gggttaaacc acaatttgca caccgtgcta taaatagaag aagagaccca tagagagcat    900
cctggttaaa caatgaacac gtttgcctga ccaattttat tatataaacc taaccatcct    960
cacaacttca agttatcatc ccctttctct tttctcctct tgttcttgtc acccgctaaa   1020
tctatcaaaa cacaagtagt cctagttgca catatattt                           1059
```

<210> SEQ ID NO 16
<211> LENGTH: 1104
<212> TYPE: DNA
<213> ORGANISM: Artificial Sequence
<220> FEATURE:
<223> OTHER INFORMATION: Synthetic Promoter
<220> FEATURE:
<221> NAME/KEY: promoter
<222> LOCATION: (1)...(114)
<223> OTHER INFORMATION: Bs3 and xa27 and Bs3-E
<220> FEATURE:
<221> NAME/KEY: misc_feature
<222> LOCATION: (734)...(781)
<223> OTHER INFORMATION: upa-AvrBs3deltarep16 box
<220> FEATURE:
<221> NAME/KEY: misc_feature
<222> LOCATION: (913)...(946)
<223> OTHER INFORMATION: upa-Avrxa27 box
<220> FEATURE:
<221> NAME/KEY: misc_feature
<222> LOCATION: (986)...(1003)
<223> OTHER INFORMATION: upa-AvrBs3 box

<400> SEQUENCE: 16

```
ctacggaata gcagcattaa ggcacatcag agatttttg ggtgttaagt ttgtcatgaa       60
acctgatgcc tccacaggaa ctgtcaatct catgtgtctt ggctctggtt ttcagaattt     120
```

-continued

```
atccagaaaa gtatcatgat aaattaatgg tgtctgtgtt tggtggctta gagtgacggc        180
tagatcaaca tctttgggat gccttgtgga gtgaaatcaa gcatacttta tcataggcga        240
aattttttgt tgtggtttgc tgcttgtaat gagagagtga tataggaagc aaatgtggag        300
atcacatttg ctcatctcct tgttgcgttg aaacttttgg tgtcaagagt tctaattcac        360
atgtatttga agattcctca tatgctgctt ttgtttctaa ttatttttc tagtaagaaa         420 acatttgttc ctgagtttcc aactagaaaa aaatatcaag taaaatagaa ttcaatcatt        480
tcccttacca acgcttggta ctgccaaccg caacaaagaa ttaatgcaaa acaacagtct        540
attaatatca acctagacta aactccttag ttttactttg aaatgcgaat gatacatgac        600
acattagatt gtacttgctt tttaccacag atacaacgat acatttgtat atctttttccc       660 ttatagcaaa ctctaatata tcatagtcaa gctaacgaaa cttatgcaag ggaaatatga        720
aattagtatg caattttatt atataaacct ctctattcca ctaaaccatc ctcacaacca        780
agtaaactca aagaactaat cattgaactg aaagatcaat atatcaaaaa aaaaaaaaaa        840
caataaaacc gtttaaccga tagattaacc atttctggtt cagtttatgg gttaaaccac        900
aatttgcaca ccgtgctata aatagaagag accaatagag agcatcctgg ttaaacaatg        960
aacacgtttg cctgaccaat tttattatat aaacctaacc atcctcacaa cttcaagtta       1020 tcatccctt tctcttttct cctcttgttc ttgtcacccg ctaaatctat caaaacacaa        1080
gtagtcctag ttgcacatat attt                                              1104
```

```
<210> SEQ ID NO 17
<211> LENGTH: 19
<212> TYPE: DNA
<213> ORGANISM: Capsicum annuum
<220> FEATURE:
<221> NAME/KEY: gene
<222> LOCATION: (0)...(0)
<223> OTHER INFORMATION: Bs3
<220> FEATURE:
<221> NAME/KEY: misc_feature
<222> LOCATION: (1)...(19)
<223> OTHER INFORMATION: upa-AvrBs3 box

<400> SEQUENCE: 17
tatataaacc taaccatcc                                                      19

<210> SEQ ID NO 18
<211> LENGTH: 15
<212> TYPE: DNA
<213> ORGANISM: Capsicum annuum
<220> FEATURE:
<221> NAME/KEY: gene
<222> LOCATION: (0)...(0)
<223> OTHER INFORMATION: Bs3-E
<220> FEATURE:
<221> NAME/KEY: misc_feature
<222> LOCATION: (1)...(15)
<223> OTHER INFORMATION: upa-AvrBs3deltarep16 box

<400> SEQUENCE: 18
tatataaacc tctct                                                          15

<210> SEQ ID NO 19
<211> LENGTH: 19
<212> TYPE: DNA
<213> ORGANISM: Capsicum annuum
<220> FEATURE:
<221> NAME/KEY: gene
<222> LOCATION: (0)...(0)
```

```
<223> OTHER INFORMATION: Bs3 upa-mut
<220> FEATURE:
<221> NAME/KEY: misc_feature
<222> LOCATION: (1)...(19)
<223> OTHER INFORMATION: upa-mut box
<220> FEATURE:
<221> NAME/KEY: misc_difference
<222> LOCATION: 1
<223> OTHER INFORMATION: A at postion 1 is a T in Bs3 UPA Box

<400> SEQUENCE: 19
aatataaacc taaccatcc                                                19

<210> SEQ ID NO 20
<211> LENGTH: 35
<212> TYPE: DNA
<213> ORGANISM: Capsicum annuum
<220> FEATURE:
<221> NAME/KEY: gene
<222> LOCATION: (0)...(0)
<223> OTHER INFORMATION: Bs3
<220> FEATURE:
<221> NAME/KEY: misc_feature
<222> LOCATION: (1)...(35)
<223> OTHER INFORMATION: Insertion comprising upa-AvrBs3 box

<400> SEQUENCE: 20
caattttatt atataaacct aaccatcctc acaac                              35

<210> SEQ ID NO 21
<211> LENGTH: 35
<212> TYPE: DNA
<213> ORGANISM: Artificial Sequence
<220> FEATURE:
<223> OTHER INFORMATION: mutated Bs3 UPA Box
<220> FEATURE:
<221> NAME/KEY: misc_feature
<222> LOCATION: (1)...(35)
<223> OTHER INFORMATION: nucleotide sequence comprising upa-mut box
<220> FEATURE:
<221> NAME/KEY: misc_difference
<222> LOCATION: (18)...(19)
<223> OTHER INFORMATION: GG at postions 18-19 is CC in upa box
<220> FEATURE:
<221> NAME/KEY: misc_difference
<222> LOCATION: (23)...(24)
<223> OTHER INFORMATION: GG at postions 23-24 is CC in upa box

<400> SEQUENCE: 21
caattttatt atataaaggt aaggatcctc acaac                              35

<210> SEQ ID NO 22
<211> LENGTH: 18
<212> TYPE: DNA
<213> ORGANISM: Oryza sativa
<220> FEATURE:
<221> NAME/KEY: gene
<222> LOCATION: (0)...(0)
<223> OTHER INFORMATION: Xa27
<220> FEATURE:
<221> NAME/KEY: misc_feature
<222> LOCATION: (1)...(18)
<223> OTHER INFORMATION: upa-AvrXa27 box

<400> SEQUENCE: 22
tagaagaaga gacccata                                                 18

<210> SEQ ID NO 23
<211> LENGTH: 34
<212> TYPE: DNA
<213> ORGANISM: Orzya sativa
```

```
<220> FEATURE:
<221> NAME/KEY: gene
<222> LOCATION: (0)...(0)
<223> OTHER INFORMATION: xa27
<220> FEATURE:
<221> NAME/KEY: misc_feature
<222> LOCATION: (1)...(34)
<223> OTHER INFORMATION: nucleotide sequence comprising the upa-Avrxa27
      box
<220> FEATURE:
<221> NAME/KEY: misc_difference
<222> LOCATION: 22
<223> OTHER INFORMATION: A at position 22 is an C in the corresponding
      position of xa27 UPA box

<400> SEQUENCE: 23
gtgctataaa tagaagagac caatagagag catc                                    34

<210> SEQ ID NO 24
<211> LENGTH: 48
<212> TYPE: DNA
<213> ORGANISM: Capsicum annuum
<220> FEATURE:
<221> NAME/KEY: gene
<222> LOCATION: (0)...(0)
<223> OTHER INFORMATION: Bs3-E
<220> FEATURE:
<221> NAME/KEY: misc_feature
<222> LOCATION: (1)...(48)
<223> OTHER INFORMATION: nucleotide sequence comprising
      upa-AvrBs3deltarep16 box

<400> SEQUENCE: 24
ttttattata taaacctctc tattccacta aaccatcctc acaaccaa                     48

<210> SEQ ID NO 25
<211> LENGTH: 13
<212> TYPE: DNA
<213> ORGANISM: Artificial Sequence
<220> FEATURE:
<223> OTHER INFORMATION: upa box consensus sequence
<220> FEATURE:
<221> NAME/KEY: misc_feature
<222> LOCATION: 11
<223> OTHER INFORMATION: n  is vaiable region that can be either 2 (nn)
      or 3 (nnn) nucleotides in length
<220> FEATURE:
<221> NAME/KEY: misc_feature
<222> LOCATION: 11
<223> OTHER INFORMATION: n is  A,T,C or G

<400> SEQUENCE: 25
tatataaacc ncc                                                           13

<210> SEQ ID NO 26
<211> LENGTH: 37
<212> TYPE: DNA
<213> ORGANISM: Capsicum annuum
<220> FEATURE:
<221> NAME/KEY: gene
<222> LOCATION: (0)...(0)
<223> OTHER INFORMATION: Bs3
<220> FEATURE:
<221> NAME/KEY: misc_feature
<222> LOCATION: (1)...(37)
<223> OTHER INFORMATION: nucleotide sequence comprising upa-AvrBs3 box

<400> SEQUENCE: 26
gcctgaccaa ttttattata taaacctaac catcctc                                 37

<210> SEQ ID NO 27
```

```
<211> LENGTH: 37
<212> TYPE: DNA
<213> ORGANISM: Artificial Sequence
<220> FEATURE:
<223> OTHER INFORMATION: Synthetic promoter element
<220> FEATURE:
<221> NAME/KEY: misc_feature
<222> LOCATION: (1)...(37)
<223> OTHER INFORMATION: nucleotide sequence comprising Bs3 upa-mut box
<220> FEATURE:
<221> NAME/KEY: misc_difference
<222> LOCATION: 17
<223> OTHER INFORMATION: A at position 17 is T in corresponding position
      of upa-AvrBs3 box

<400> SEQUENCE: 27
gcctgaccaa ttttataata taaacctaac catcctc                              37

<210> SEQ ID NO 28
<211> LENGTH: 25
<212> TYPE: DNA
<213> ORGANISM: Oryza sativa
<220> FEATURE:
<221> NAME/KEY: gene
<222> LOCATION: (0)...(0)
<223> OTHER INFORMATION: Os8N3
<220> FEATURE:
<221> NAME/KEY: misc_feature
<222> LOCATION: (1)...(25)
<223> OTHER INFORMATION: upa-PthXo1 box

<400> SEQUENCE: 28
tgcatctccc cctactgtac accac                                           25

<210> SEQ ID NO 29
<211> LENGTH: 24
<212> TYPE: DNA
<213> ORGANISM: Oryza sativa
<220> FEATURE:
<221> NAME/KEY: gene
<222> LOCATION: (0)...(0)
<223> OTHER INFORMATION: OstFX1
<220> FEATURE:
<221> NAME/KEY: misc_feature
<222> LOCATION: (1)...(24)
<223> OTHER INFORMATION: upa-PthXo6 box

<400> SEQUENCE: 29
tataaaaggc cctcaccaac ccat                                            24

<210> SEQ ID NO 30
<211> LENGTH: 23
<212> TYPE: DNA
<213> ORGANISM: Oryza sativa
<220> FEATURE:
<221> NAME/KEY: gene
<222> LOCATION: (0)...(0)
<223> OTHER INFORMATION: OsTFIIAgamma
<220> FEATURE:
<221> NAME/KEY: misc_feature
<222> LOCATION: (1)...(23)
<223> OTHER INFORMATION: upa-PthXo7 box

<400> SEQUENCE: 30
tataatcccc aaatcccctc ctc                                             23

<210> SEQ ID NO 31
<211> LENGTH: 24
<212> TYPE: DNA
<213> ORGANISM: Oryza sativa
<220> FEATURE:
```

```
<221> NAME/KEY: gene
<222> LOCATION: (0)...(0)
<223> OTHER INFORMATION: OsTFX1
<220> FEATURE:
<221> NAME/KEY: misc_feature
<222> LOCATION: (1)...(24)
<223> OTHER INFORMATION: UPT-PthX06 box

<400> SEQUENCE: 31
tataaaaggc cctcaccaac ccat                                              24

<210> SEQ ID NO 32
<211> LENGTH: 27
<212> TYPE: DNA
<213> ORGANISM: Oryza sativa
<220> FEATURE:
<221> NAME/KEY: gene
<222> LOCATION: (0)...(0)
<223> OTHER INFORMATION: Os11N3
<220> FEATURE:
<221> NAME/KEY: misc_feature
<222> LOCATION: (1)...(27)
<223> OTHER INFORMATION: UPT-AvrXa7 box

<400> SEQUENCE: 32
tatataaacc ccctccaacc aggtgct                                           27

<210> SEQ ID NO 33
<211> LENGTH: 24
<212> TYPE: DNA
<213> ORGANISM: Oryza sativa
<220> FEATURE:
<221> NAME/KEY: gene
<222> LOCATION: (0)...(0)
<223> OTHER INFORMATION: OsXa13
<220> FEATURE:
<221> NAME/KEY: misc_feature
<222> LOCATION: (1)...(24)
<223> OTHER INFORMATION: UPT-PthXo1 box

<400> SEQUENCE: 33
gcatctcccc ctactgtaca ccac                                              24

<210> SEQ ID NO 34
<211> LENGTH: 963
<212> TYPE: DNA
<213> ORGANISM: Artificial Sequence
<220> FEATURE:
<223> OTHER INFORMATION: synthetic pathogen-inducible promoter
<220> FEATURE:
<221> NAME/KEY: misc_feature
<222> LOCATION: (302)...(307)
<223> OTHER INFORMATION: AgeI site
<220> FEATURE:
<221> NAME/KEY: misc_feature
<222> LOCATION: (802)...(807)
<223> OTHER INFORMATION: XhoI site
<220> FEATURE:
<221> NAME/KEY: misc_feature
<222> LOCATION: (328)...(346)
<223> OTHER INFORMATION: UPT-Apl1 box
<220> FEATURE:
<221> NAME/KEY: misc_feature
<222> LOCATION: (362)...(378)
<223> OTHER INFORMATION: UPT-Apl2 box
<220> FEATURE:
<221> NAME/KEY: misc_feature
<222> LOCATION: (394)...(418)
<223> OTHER INFORMATION: UPT-Apl3 box
<220> FEATURE:
<221> NAME/KEY: misc_feature
<222> LOCATION: (434)...(452)
<223> OTHER INFORMATION: UPT-PthB box
```

```
<220> FEATURE:
<221> NAME/KEY: misc_feature
<222> LOCATION: (469)...(487)
<223> OTHER INFORMATION: UPT-PthAasterisk box
<220> FEATURE:
<221> NAME/KEY: misc_feature
<222> LOCATION: (503)...(518)
<223> OTHER INFORMATION: UPT-PthAasterisk2
<220> FEATURE:
<221> NAME/KEY: misc_feature
<222> LOCATION: (534)...(552)
<223> OTHER INFORMATION: UPT-PthAw box
<220> FEATURE:
<221> NAME/KEY: misc_feature
<222> LOCATION: (568)...(585)
<223> OTHER INFORMATION: UPT-PthA1 box
<220> FEATURE:
<221> NAME/KEY: misc_feature
<222> LOCATION: (601)...(617)
<223> OTHER INFORMATION: UPT-PthA2 box
<220> FEATURE:
<221> NAME/KEY: misc_feature
<222> LOCATION: (633)...(649)
<223> OTHER INFORMATION: UPT-PthA3 box
<220> FEATURE:
<221> NAME/KEY: misc_feature
<222> LOCATION: (665)...(687)
<223> OTHER INFORMATION: UPT-pB3.7 box
<220> FEATURE:
<221> NAME/KEY: misc_feature
<222> LOCATION: (703)...(718)
<223> OTHER INFORMATION: UPT-HssB3.0 box
<220> FEATURE:
<221> NAME/KEY: misc_feature
<222> LOCATION: (734)...(752)
<223> OTHER INFORMATION: UPT-PthA box
<220> FEATURE:
<221> NAME/KEY: misc_feature
<222> LOCATION: (768)...(786)
<223> OTHER INFORMATION: UPT-PthC box
<220> FEATURE:
<221> NAME/KEY: misc_feature
<222> LOCATION: (844)...(861)
<223> OTHER INFORMATION: upa-AvrBs3 box

<400> SEQUENCE: 34
ttagttttac tttgaaatgc gaatgataca tgacacatta gattgtactt gcttttacc      60 acagatacaa cgatacattt gtatatcttt tcccttatag caaactctaa tatatcatag    120
tcaagctaac gaaacttatg caagggaaat atgaaattag tatgcaagta aactcaaaga    180
actaatcatt gaactgaaag atcaatatat caaaaaaaaa aaaaaacaat aaaaccgttt    240
aaccgataga ttaaccattt ctggttcagt ttatgggtta aaccacaatt tgcacaccct    300
gaccggttta gttttacttt gaaatgctat aaacctcttt taccttgaat gatacatgac    360
atatacacct cttttactca ttagattgta ctttacacac ctcctaccac ctctacttgc    420
tttttaccac agatctctat ctcaacccct tttacaacga tacatttgta tacacctctt    480
tacattttat atcttttccc tttatatacc tacaccctat agcaaactct aattatttac    540
cactcttacc ttatatcata gtcaagctat ataacctacac taccttaacg aaacttatgc    600
tacacacctc ttttaataag ggaaatatga atacacatc tttaaaactt tagtatgcaa    660
gtaatatata cctacactac actacctact caaagaacta attacacatt ataccactca    720
ttgaactgaa agatataaat ctctttacc ttcaatata tcaaaaatct ctatataact    780
ccctttaaaa aaaacaata actcgaggtt aaacaatgaa cacgtttgcc tgaccaattt    840
tattatataa acctaaccat cctcacaact tcaagttatc atcccctttc tcttttctcc    900
tcttgttctt gtcacccgct aaatctatca aaacacaagt agtcctagtt gcacatatat    960
```

-continued ttc                                                                963

<210> SEQ ID NO 35
<211> LENGTH: 19
<212> TYPE: DNA
<213> ORGANISM: Artificial Sequence
<220> FEATURE:
<223> OTHER INFORMATION: predicted UPT-Apl1 box

<400> SEQUENCE: 35
tataaacctc ttttaccttt                                               19

<210> SEQ ID NO 36
<211> LENGTH: 17
<212> TYPE: DNA
<213> ORGANISM: Artificial Sequence
<220> FEATURE:
<223> OTHER INFORMATION: predicted UPT-Apl2 box

<400> SEQUENCE: 36
tatacacctc ttttact                                                  17

<210> SEQ ID NO 37
<211> LENGTH: 25
<212> TYPE: DNA
<213> ORGANISM: Artificial Sequence
<220> FEATURE:
<223> OTHER INFORMATION: predicted UPT-Apl3 box

<400> SEQUENCE: 37
tacacacctc ctaccacctc tactt                                         25

<210> SEQ ID NO 38
<211> LENGTH: 19
<212> TYPE: DNA
<213> ORGANISM: Artificial Sequence
<220> FEATURE:
<223> OTHER INFORMATION: predicted UPT-PthB box

<400> SEQUENCE: 38
tctctatctc aacccsctttt                                              19

<210> SEQ ID NO 39
<211> LENGTH: 19
<212> TYPE: DNA
<213> ORGANISM: Artificial Sequence
<220> FEATURE:
<223> OTHER INFORMATION: predicted UPT-PthAasterisk box

<400> SEQUENCE: 39
tatacacctc tttacattt                                                19

<210> SEQ ID NO 40
<211> LENGTH: 16
<212> TYPE: DNA
<213> ORGANISM: Artificial Sequence
<220> FEATURE:
<223> OTHER INFORMATION: predicted UPT-PthAasterisk2 box

<400> SEQUENCE: 40
tatataccta caccct                                                   16

<210> SEQ ID NO 41
<211> LENGTH: 19
<212> TYPE: DNA
<213> ORGANISM: Artificial Sequence

```
<220> FEATURE:
<223> OTHER INFORMATION: predicted UPT-PthAw box

<400> SEQUENCE: 41
tatttaccac tcttacctt                                              19

<210> SEQ ID NO 42
<211> LENGTH: 18
<212> TYPE: DNA
<213> ORGANISM: Artificial Sequence
<220> FEATURE:
<223> OTHER INFORMATION: predicted UPT-PthA1 box

<400> SEQUENCE: 42
tatataccta cactacct                                               18

<210> SEQ ID NO 43
<211> LENGTH: 17
<212> TYPE: DNA
<213> ORGANISM: Artificial Sequence
<220> FEATURE:
<223> OTHER INFORMATION: predicted UPT-PthA2 box

<400> SEQUENCE: 43
tacacacctc ttttaat                                                17

<210> SEQ ID NO 44
<211> LENGTH: 17
<212> TYPE: DNA
<213> ORGANISM: Artificial Sequence
<220> FEATURE:
<223> OTHER INFORMATION: predicted UPT-PthA3 box

<400> SEQUENCE: 44
tacacatctt taaaact                                                17

<210> SEQ ID NO 45
<211> LENGTH: 23
<212> TYPE: DNA
<213> ORGANISM: Artificial Sequence
<220> FEATURE:
<223> OTHER INFORMATION: predicted UPT-pB3.7 box

<400> SEQUENCE: 45
tatataccta cactacacta cct                                         23

<210> SEQ ID NO 46
<211> LENGTH: 16
<212> TYPE: DNA
<213> ORGANISM: Artificial Sequence
<220> FEATURE:
<223> OTHER INFORMATION: predicted UPT-HssB3.0 box

<400> SEQUENCE: 46
tacacattat accact                                                 16

<210> SEQ ID NO 47
<211> LENGTH: 19
<212> TYPE: DNA
<213> ORGANISM: Artificial Sequence
<220> FEATURE:
<223> OTHER INFORMATION: predicted UPT-PthA box

<400> SEQUENCE: 47
tataaatctc ttttaccit                                              19
```

```
<210> SEQ ID NO 48
<211> LENGTH: 19
<212> TYPE: DNA
<213> ORGANISM: Artificial Sequence
<220> FEATURE:
<223> OTHER INFORMATION: predicted UPT-PthC box

<400> SEQUENCE: 48
tctctatata actcccttt                                                19
```

PATHOGEN-INDUCIBLE PROMOTERS AND THEIR USE IN ENHANCING THE DISEASE RESISTANCE OF PLANTS

CROSS-REFERENCE TO RELATED APPLICATIONS

This application claims the benefit of U.S. Provisional Patent Application No. 61/113,206, filed Nov. 10, 2008.

BACKGROUND OF THE INVENTION

Plants are hosts to thousands of infectious diseases caused by a vast array of phytopathogenic fungi, bacteria, viruses, oomycetes and nematodes. Plants recognize and resist many invading phytopathogens by inducing a rapid defense response. Recognition is often due to the interaction between a dominant or semi-dominant resistance (R) gene product in the plant and a corresponding dominant avirulence (Avr) gene product expressed by the invading phytopathogen. R-gene triggered resistance often results in a programmed cell-death, which has been termed the hypersensitive response (HR). The HR is believed to constrain spread of the pathogen.

How R gene products mediate perception of the corresponding Avr proteins is mostly unclear. It has been proposed that phytopathogen Avr products function as ligands, and that plant R gene products function as receptors. In this receptor-ligand model binding of the Avr product to a corresponding R gene product in the plant initiates the chain of events within the plant that produces HR leads to disease resistance. In an alternate model the R protein perceives the action rather than the structure of the Avr protein. In this model the Avr protein is believed to modify a plant target protein (pathogenicity target) in order to promote pathogen virulence. The modification of the pathogenicity protein is detected by the matching R protein and triggers a defense response. Experimental evidence suggests that some R proteins act as Avr receptors while others detect the activity of the Avr protein.

The production of transgenic plants carrying a heterologous gene sequence is now routinely practiced by plant molecular biologists. Methods for incorporating an isolated gene sequence into an expression cassette, producing plant transformation vectors, and transforming many types of plants are well known. Examples of the production of transgenic plants having modified characteristics as a result of the introduction of a heterologous transgene include: U.S. Pat. No. 5,719,046 to Guerineau (production of herbicide resistant plants by introduction of bacterial dihydropteroate synthase gene); U.S Pat. No. 5,231,020 to Jorgensen (modification of flavenoids in plants); U.S. Pat. No. 5,583,021 to Dougherty (production of virus resistant plants); and U.S. Pat. No. 5,767,372 to De Greve and U.S. Pat. No. 5,500,365 to Fischoff (production of insect resistant plants by introducing *Bacillus thuringiensis* genes).

In conjunction with such techniques, the isolation of plant R genes has similarly permitted the production of plants having enhanced resistance to certain pathogens. Since the cloning of the first R gene, Pto from tomato, which confers resistance to *Pseudomonas syringae* pv. *tomato* (Martin et al. (1993) *Science* 262: 1432-1436), a number of other R genes have been reported (Liu et al. (2007) *J. Genet. Genomics* 34:765-776). A number of these genes have been used to introduce the encoded resistance characteristic into plant lines that were previously susceptible to the corresponding pathogen. For example, U.S. Pat. No. 5,571,706 describes the introduction of the N gene into tobacco lines that are susceptible to Tobacco Mosaic Virus (TMV) in order to produce TMV-resistant tobacco plants. WO 95/28423 describes the creation of transgenic plants carrying the Rps2 gene from *Arabidopsis thaliana*, as a means of creating resistance to bacterial pathogens including *Pseudomonas syringae*, and WO 98/02545 describes the introduction of the Prf gene into plants to obtain broad-spectrum pathogen resistance.

Bacterial spot disease of tomato and pepper, caused by the phytopathogenic bacterium *Xanthomonas campestris* pv. *vesicatoria* (Xcv), can be devastating to commercial production of these crops in areas of the world with high humidity and heavy rainfall. While control of Xcv in commercial agriculture is based largely on the application of pesticides, genetic resistance to bacterial spot disease has been described in both tomato and pepper (Cook and Stall (1963) *Phytopathology* 53: 1060-1062; Cook and Guevara (1984) *Plant Dis.* 68: 329-330; Kim and Hartman (1985) *Plant Dis.* 69: 233-235; Jones and Scott (1986) *Plant Dis.* 70: 337-339). Of the two hosts, genetic resistance in pepper has been better characterized. Several single loci (Bs1, Bs2, and Bs3) that confer resistance in a "gene-for-gene" manner have been identified (Hibberd et al. (1987) *Phytopathology* 77: 1304-1307). Moreover, the corresponding avirulence genes (avrBs1, avrBs2, and avrBs3) have been cloned from Xcv (Swanson et al. (1988) *Mol. Plant-Microbe Interact.* 1:5-9; Minsavage et al. (1990) *Mol. Plant-Microbe Interact.* 3: 41-47). Genetic and molecular characterization of these avirulence genes has provided a great deal of information concerning the interaction between Xcv and pepper (Kearney et al. (1988) *Nature* 332: 541-543; Kearney and Staskawicz (1990) *Nature* 346: 385-386; Herbers et al. (1992) *Nature* 356: 172-174; Van der Ackerveken et al. (1992) *Plant J.* 2: 359-366). More recently, the Bs3 gene of pepper has been isolated and sequenced (U.S. Pat. No. 6,262,343)

Xcv employs a type III secretion (T3S) system to inject an arsenal of about 20 effector proteins into the host cytoplasm that collectively promote virulence (Thieme et al. (2005) *J. Bacteriol.* 187:7254). R protein mediated defense in response to Xcv effector proteins is typically accompanied by a programmed cell death response referred to as the HR. AvrBs3 is one Avr protein that R proteins recognize and is a member of large family (>100 sequenced members) of highly related bacterial effector proteins that are present in various *Xanthomonas* and *Ralstonia solanacearum* strains (Schornack et al. (2006) *J. Plant Physiol.* 163:256). Due to their structural relatedness to eukaryotic transcription factors AvrBs3-like proteins are also referred to as TAL (transcription activator like) effectors. The most characteristic feature of TAL effectors is the central repeat domain that consists of a variable number (1.5-28.5) of tandem-arranged, almost identical 34/35-(*Xanthomonas/Ralstonia*) repeat units. Analysis of AvrBs3 from Xcv has shown that the repeat domain mediates specific binding to a promoter element that has been termed "upa box" (Kay et al. (2007) *Science* 318:648-651). The full length AvrBs3 protein not only binds to promoters with a upa box but also transcriptionally activates these promoters. In pepper genotypes that are susceptible to Xcv, AvrBs3 binds to and activates the promoter of the upa20 gene, which causes cell hypertrophy (Kay et al. (2007) *Science* 318:648-651). In pepper plants that contain the Bs3 resistance gene, AvrBs3 triggers a cell death response (i.e., HR) that restricts pathogen growth. Molecular analysis revealed that the Bs3 promoter contains, like the upa20 promoter, a upa box. AvrBs3 binds to and transcriptionally activates the pepper Bs3 promoter thereby triggering a defense reaction (Römer et al. (2007) *Science* 318:645-648). Thus the Bs3 promoter represents a DNA-based decoy receptor. The AvrBs3-deletion derivative AvrBs3Δrep16 (lacks repeat units 11-14) does not activate the Bs3 promoter but its allelic variant Bs3-E (Römer et al. (2007) *Science* 318:645-648). Intriguingly the Bs3 and Bs3-E promoter differ in their upa boxes (herein referred to as "upa$_{AvrBs3}$" and "upa$_{AvrBs3\Delta rep16}$" boxes, respectively). Thus recognition specificity of TAL effectors is determined by a) the sum of the repeat units of a given TAL effector and b) the upa box of a given host promoter.

The TAL effector AvrXa27 from the bacterial rice pathogen *Xanthomonas oryzae* pv. *oryzae* (Xoo) activates the promoter of the matching rice R gene, Xa27 (Gu et al. (2005) *Nature* 435:1122-1125). Thus, the R genes Bs3 and Xa27 are both transcriptionally activated by their matching TAL effectors and thus are identical in their mechanisms of activation. However, the predicted Bs3 and Xa27 proteins share neither sequence homology to each other nor to the classical NB-LRR type R proteins. Nevertheless, it seems likely that AvrXa27- and AvrBs3-mediated activation of host promoters are mechanistically similar. To date, no report has yet appeared which provides evidence demonstrating that AvrXa27 binds to the Xa27 promoter and that the Xa27 promoter contains a upa box to which AvrXa27 binds.

BRIEF SUMMARY OF THE INVENTION

Methods are provided for making pathogen-inducible promoters that find use in the expression of genes in plants following attacks from plant pathogens. The methods of the invention involve producing a pathogen-inducible promoter comprising one, two, three, or more upa boxes. By using two or more upa boxes that bind to TAL effectors from different plant pathogens, particularly bacterial plant pathogens, the methods can be used to make promoters that are inducible by two or more plant pathogens.

Methods are also provided for making an R gene, which finds use in increasing the resistance of plants to plant pathogens. The methods of the invention involve producing a nucleic acid construct comprising a pathogen-inducible promoter operably linked to a coding sequence of an R gene product. The pathogen-inducible promoter is made by the methods disclosed herein and comprises one, two, three, or more upa boxes. In one embodiment of the invention, the methods are used to produce an R gene that is inducible by two or more plant pathogens. Such an R gene of the present invention comprises a promoter having two or more upa boxes, with each upa box being inducible by a different plant pathogen, particularly a bacterial plant pathogen that produces a TAL effector.

Methods are further provided for identifying a upa box in the promoter of a gene from a plant. The methods involve exposing a plant, plant part, or plant cell to a TAL effector and then identifying two or more genes in the plant, plant part, or plant cell, wherein the expression of these genes is directly induced following exposure to said TAL effector. The methods further involve comparing the promoters of the two or more genes to identify one or more nucleotide sequences comprising a potential upa box, assaying any such nucleotide sequence for upa-box activity. Finally, the methods involve identifying a upa box as a nucleotide sequence that comprises upa-box activity.

Additionally provided are isolated nucleic acid molecules, expressions cassettes, nucleic acid or polynucleotide constructs, plants, plant parts, plant cells, seeds, and non-human host cells comprising the pathogen-inducible promoters, upa boxes, and R genes of the present invention.

SEQUENCE LISTING

Figure 1:
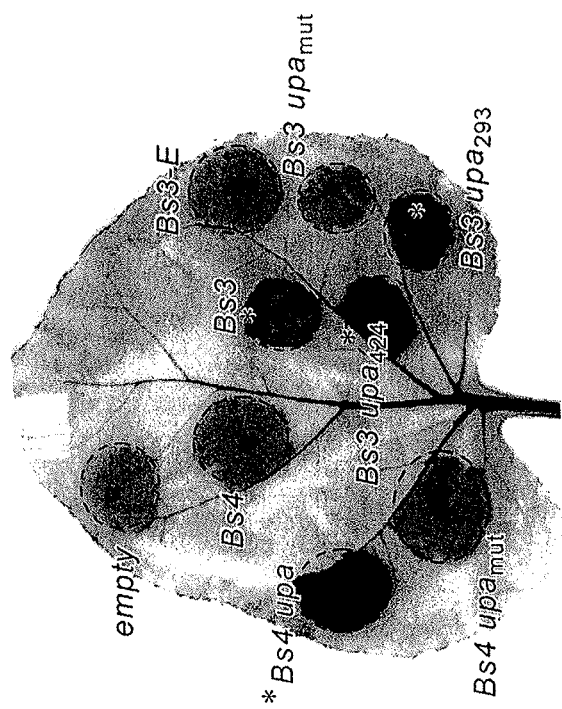
FIG. 1A. Schematic representation of the constructs that were used to study functionality of the upa box. Hatched and white boxes represent the Bs3/Bs3-E promoter and the Bs4 promoters respectively. Small black and gray boxes represent the upa$_{AvrBs3}$ and upa$_{AvrBs3\Delta rep16}$ boxes, respectively. Please note that the Bs3 and Bs3-E promoters differ only within these boxes but are otherwise identical and are therefore displayed. A white line within the upa$_{AvrBs3}$ box marks a mutation in this box. Numbers adjacent to the upa boxes define their distance to the ATG start codon. Gray rectangles represent the coding region of the Bs3 gene.
FIG. 1B. Functional analysis of different Bs3 and Bs4 promoter derivatives. The depicted promoter derivatives were delivered together with a 35S-driven avrBs3 gene into *Nicotiana benthamiana* leaves via *Agrobacterium tumefaciens* (OD600=0.8). Dashed lines mark the inoculated areas. Four days after infiltration, the leaves were cleared to visualize the HR (dark areas). Please note, that delivery of a 35S-driven avrBs3 does trigger on its own a weak reaction (see 'empty'). Thus, only dark areas (marked with an asterisk [*]) represent functional promoters.
Figure 1:
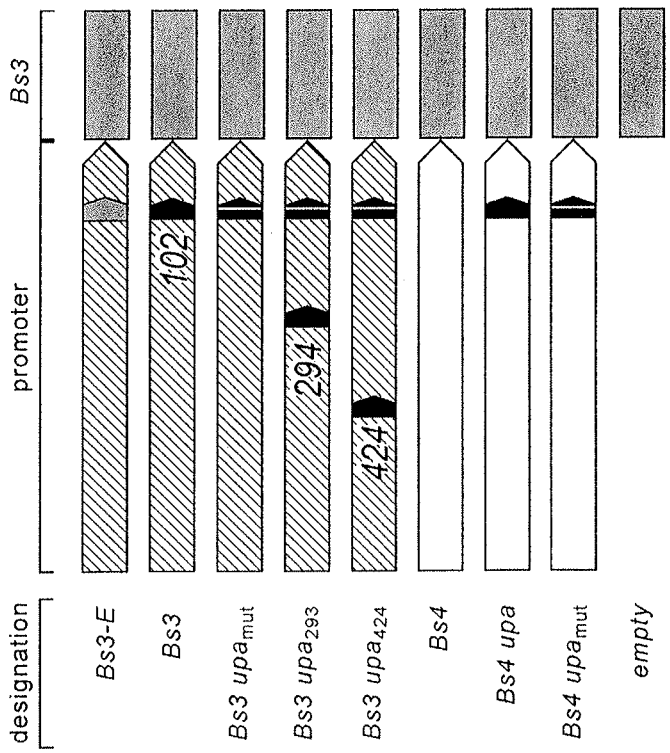

The nucleotide and amino acid sequences listed in the accompanying sequence listing are shown using standard letter abbreviations for nucleotide bases, and three-letter code for amino acids. The nucleotide sequences follow the standard convention of beginning at the 5' end of the sequence and proceeding forward (i.e., from left to right in each line) to the 3' end. Only one strand of each nucleic acid sequence is shown, but the complementary strand is understood to be included by any reference to the displayed strand. The amino acid sequences follow the standard convention of beginning at the amino terminus of the sequence and proceeding forward (i.e., from left to right in each line) to the carboxy terminus.

SEQ ID NO: 1 sets forth a nucleotide sequence comprising the coding sequence of the pepper Bs3 gene. The nucleotide sequence can be found in Accession No. EU078684.

SEQ ID NO: 2 sets forth a nucleotide sequence comprising the coding sequence of the tomato Bs4 gene. The nucleotide sequence can be found in Accession No. AY438027.

SEQ ID NO: 3 sets forth a nucleotide sequence comprising the promoter of the Bs3 gene. The nucleotide sequence can be found in Accession No. EU078684.

SEQ ID NO: 4 sets forth a nucleotide sequence comprising the promoter of the Bs3-E allele of the Bs3 gene. The nucleotide sequence can be found in Accession No. EU078683.

SEQ ID NO: 5 sets forth the nucleotide sequence of the Bs3 upa$_{mut}$ promoter.

SEQ ID NO: 6 sets forth the nucleotide sequence of the Bs3 upa$_{294}$ promoter.

SEQ ID NO: 7 sets forth the nucleotide sequence of the Bs3 upa$_{424}$ promoter.

SEQ ID NO: 8 sets forth a nucleotide sequence comprising the promoter of the Bs4 gene. The nucleotide sequence can be found in Accession No. AY438027.

SEQ ID NO: 9 sets forth the nucleotide sequence of the Bs4 upa promoter.

SEQ ID NO: 10 sets forth the nucleotide sequence of the Bs4 upa$_{mut}$ promoter.

SEQ ID NO: 11 sets forth a nucleotide sequence comprising the promoter of the rice Xa27 gene. The nucleotide sequence can be found in Accession No. AY986492.

SEQ ID NO: 12 sets forth a nucleotide sequence comprising the promoter of the rice xa27 gene. The nucleotide sequence can be found in Accession No. AY986491.

SEQ ID NO: 13 sets forth the nucleotide sequence of the Bs3+Bs3-E promoter.

SEQ ID NO: 14 sets forth the nucleotide sequence of the Bs3+Xa27+Bs3-E promoter.

SEQ ID NO: 15 sets forth the nucleotide sequence of the Bs3+Xa27 promoter.

SEQ ID NO: 16 sets forth the nucleotide sequence of the Bs3+xa27+Bs3-E promoter.

SEQ ID NO: 17 sets forth the nucleotide sequence of the upa$_{AvrBs3}$ box.

SEQ ID NO: 18 sets forth the nucleotide sequence of the upa$_{AvrBs3\Delta rep16}$ box.

SEQ ID NO: 19 sets forth the nucleotide sequence of the Bs3 upa$_{mut}$ box.

SEQ ID NO: 20 sets forth a nucleotide sequence comprising the upa$_{AvrBs3}$ box.

SEQ ID NO: 21 sets forth a nucleotide sequence comprising a mutated upa$_{AvrBs3}$ box.

SEQ ID NO: 22 sets forth the nucleotide sequence of the upa$_{AvrXa27}$ box.

SEQ ID NO: 23 sets forth a nucleotide sequence comprising the upa$_{AvrXa27}$ box.

SEQ ID NO: 24 sets forth a nucleotide sequence comprising the upa$_{AvrBs3\Delta rep16}$ box.

SEQ ID NO: 25 sets forth the consensus nucleotide sequence of the upa box, a conserved DNA element that was shown to be bound by AvrBs3 by Kay et al. (2007) Science 318(5850): 648-651.

SEQ ID NO: 26 sets forth a nucleotide sequence comprising the upa$_{AvrBs3}$ box.

SEQ ID NO: 27 sets forth a nucleotide sequence comprising the upa$_{AvrBs3\Delta rep16}$ box.

SEQ ID NO: 28 sets forth the nucleotide sequence of the upa$_{PthXo1}$ box.

SEQ ID NO: 29 sets forth the nucleotide sequence of the upa$_{PthXo6}$ box.

SEQ ID NO: 30 sets forth the nucleotide sequence of the upa$_{PthXo7}$ box.

SEQ ID NO: 31 sets forth the nucleotide sequence of the UPT$_{PthXo6}$ box of the rice OsTFX1 gene.

SEQ ID NO: 32 sets forth the nucleotide sequence of the UPT$_{AvrXa7}$ box of the rice Os11N3 gene.

SEQ ID NO: 33 sets forth the nucleotide sequence of the UPT$_{PthXo1}$ box of the rice OsXa13 gene.

SEQ ID NO: 34 sets forth the nucleotide sequence of the complex promoter disclosed in Example 8.

SEQ ID NO: 35 sets forth the nucleotide sequence of the UPT$_{Apl1}$ box used in the complex promoter comprising the nucleotide sequence set forth in SEQ ID NO: 34.

SEQ ID NO: 36 sets forth the nucleotide sequence of the UPT$_{Apl2}$ box used in the complex promoter comprising the nucleotide sequence set forth in SEQ ID NO: 34.

SEQ ID NO: 37 sets forth the nucleotide sequence of the UPT$_{Apl3}$ box used in the complex promoter comprising the nucleotide sequence set forth in SEQ ID NO: 34.

SEQ ID NO: 38 sets forth the nucleotide sequence of the UPT$_{PthB}$ box used in the complex promoter comprising the nucleotide sequence set forth in SEQ ID NO: 34.

SEQ ID NO: 39 sets forth the nucleotide sequence of the UPT$_{PthA*}$ box used in the complex promoter comprising the nucleotide sequence set forth in SEQ ID NO: 34.

SEQ ID NO: 40 sets forth the nucleotide sequence of the UPT$_{PthA*2}$ box used in the complex promoter comprising the nucleotide sequence set forth in SEQ ID NO: 34.

SEQ ID NO: 41 sets forth the nucleotide sequence of the UPT$_{PthAw}$ box used in the complex promoter comprising the nucleotide sequence set forth in SEQ ID NO: 34.

SEQ ID NO: 42 sets forth the nucleotide sequence of the UPT$_{PthA1}$ box used in the complex promoter comprising the nucleotide sequence set forth in SEQ ID NO: 34.

SEQ ID NO: 43 sets forth the nucleotide sequence of the UPT$_{PthA2}$ box used in the complex promoter comprising the nucleotide sequence set forth in SEQ ID NO: 34.

SEQ ID NO: 44 sets forth the nucleotide sequence of the UPT$_{PthA3}$ box used in the complex promoter comprising the nucleotide sequence set forth in SEQ ID NO: 34.

SEQ ID NO: 45 sets forth the nucleotide sequence of the UPT$_{pB3.7}$ box used in the complex promoter comprising the nucleotide sequence set forth in SEQ ID NO: 34.

SEQ ID NO: 46 sets forth the nucleotide sequence of the UPT$_{HssB3.0}$ box used in the complex promoter comprising the nucleotide sequence set forth in SEQ ID NO: 34.

SEQ ID NO: 47 sets forth the nucleotide sequence of the UPT$_{PthA}$ box used in the complex promoter comprising the nucleotide sequence set forth in SEQ ID NO: 34.

SEQ ID NO: 48 sets forth the nucleotide sequence of the UPT$_{PthC}$ box used in the complex promoter comprising the nucleotide sequence set forth in SEQ ID NO: 34.

DETAILED DESCRIPTION OF THE INVENTION

Recently, the pepper (*Capsicum annuum*) Bs3 resistance (R) gene was isolated, sequenced, and characterized. See, Römer et al. (2007) *Science* 318:645-648, U.S. Patent Application Publication No. 2009/0133158, and WO 2009/042753; all of which are hereby incorporated in their entirety by reference. Molecular analysis revealed that the Bs3 promoter contains an element known as a upa box and that the bacterial effector protein AvrBs3 binds to the upa box and activates the Bs3 promoter.

The present invention is based on several discoveries as disclosed hereinbelow that were made during the further characterization of the upa box of the Bs3 promoter (referred to herein as $upa_{AvrBs3}$) and the upa boxes of the pepper Bs3-E promoter (referred to herein as $upa_{AvrBs3\Delta rep16}$) and the rice (*Oryza sativa*) Xa27 promoter (referred to herein as $upa_{AvrXa27}$). First, the function or biological activity of the $upa_{AvrBs3}$ box was found not to depend on its position within the Bs3 promoter. Second, the function or biological activity of the $upa_{AvrBs3}$ box is not dependent on being within the Bs3 promoter. That is the $upa_{AvrBs3}$ was discovered to function in the same or similar manner when inserted into a promoter other than the Bs3 promoter. Third, the combination of the TAL effector, AvrXa27, and the promoter of the R gene Xa27 can functionally replace AvrBs3 and the Bs3 promoter. This discovery is based on the results of an experiment (see, Example 3 below) involving the construction of a fusion gene comprising the Xa27 promoter operably linked to a nucleotide sequence encoding Bs3. After this construct was co-delivered to *Nicotiana benthamiana* leaves with a nucleotide sequence comprising a constitutive promoter operably linked to an avrXa27 coding sequence, a hypersensitive response was observed in the leaves. Fourth, functionally relevant nucleotide polymorphisms between the Xa27 and xa27 promoters are located adjacent to the predicted TATA box of these promoters. This discovery reveals that $upa_{AvrXa27}$ is found near the vicinity for the TATA box in the Xa27 promoter. Fifth, the upa boxes of the Bs3, Bs3-E and Xa27 promoters can be functionally combined in one complex promoter. This discovery reveals that upa boxes from three or more different R genes that are each specific for TAL effectors from different plant pathogens can be combined into a single promoter that is directly inducible by the TAL effectors of the different pathogens.

The present invention provides methods for making a pathogen-inducible promoter. The methods comprise producing a nucleic acid molecule that comprise a nucleotide sequence having a 5' end nucleotide and a 3' end nucleotide, wherein the nucleotide sequence comprises at least one upa box having a 5' end nucleotide and a 3' end nucleotide, and wherein said 3' end nucleotide of said upa box is not said 3' end nucleotide of said nucleotide sequence. A pathogen-inducible promoter produced by the methods of the invention is capable of driving pathogen-inducible expression of a polynucleotide that is operably linked to the said 3' end of the promoter sequence. Such promoters find use in driving the pathogen-inducible expression of an operably linked polynucleotide particularly a polynucleotide encoding an R gene product.

For the present invention, "upa box" is intended to mean a promoter element that specifically binds with an AvrBs3-like protein, also referred to as a TAL effector, and that a promoter comprising such a upa box is capable, in the presence of its TAL effector, of inducing or increasing the expression of an operably linked nucleic acid molecule. Recently, such "upa boxes" have been referred to as "UPT boxes," where "UPT" stands for "UPregulated by TAL effectors" (Römer et al. (2009) *Proc. Natl. Acad. Sci. USA*, in press). Unless stated otherwise or readily apparent from the context, "upa box" and "UPT box" as used herein are equivalent terms that can be used interchangeably and that do not differ in meaning and/or scope.

The methods disclosed herein do not depend on the upa box being in a particular position for the upa box to function within a pathogen-inducible promoter of the present invention. However, the position of the 3' end nucleotide of the upa box is at least about one nucleotide from the 3' end nucleotide of the nucleotide sequence of the promoter. In embodiments of the invention, at least 2, 5, 10, 25, 50, 100, 125, 150, 200, 300, 500, 750, 1000, or more nucleotides separate the 3' end nucleotide of the upa box and the 3' end nucleotide of the promoter of the invention. In a preferred embodiment of the invention, the 3' end nucleotide of the upa box is at least about 50 nucleotides from the 3' end nucleotide of the promoter or at least about 50 nucleotides upstream of the transcriptional start site. In one embodiment, the 5' end nucleotide of the upa box is the 5' end nucleotide of the promoter nucleotide sequence. In other embodiments, the 5' end nucleotide of the upa box is 1, 2, 5, 10, 25, 50, 100, 125, 150, 200, 300, 500, 750, 1000, or more nucleotides 3' of the 5' end of the promoter nucleotide sequence.

By "producing a nucleic acid molecule" is intended the making of a nucleic acid molecule by any known methods including, but not limited to, chemical synthesis of the entire nucleic acid molecule or parts or parts thereof, modification of a pre-existing nucleic acid molecule, such as, for example, a DNA molecule comprising the promoter of an Bs3 or other R gene, by molecular biology methods such as, for example, restriction endonuclease digestion and ligation, and the combination of chemical synthesis and modification.

The methods of the present invention can be used to make pathogen-inducible promoters comprising at least two upa boxes, particularly pathogen-inducible promoters comprising 1, 2, 3, 4, 5, 6, 7, 8, 9, 10, 11, 12, 13, 14, 15, 16, 17, 18, 19, 20, or more upa boxes. In such methods, the first of the at least two upa boxes has a 5' end nucleotide and a 3' end nucleotide and the second and any additional two upa boxes each have a 5' end nucleotide and a 3' end nucleotide. The first upa box is positioned within the promoter, 3' of the second and any additional upa boxes. For any promoter of the present invention comprising two or more upa boxes, any of the two or more upa boxes can be identical to each other, but preferably, each of the two or more upa boxes is different from the other upa boxes and is capable of inducing expression in response to a different TAL effector.

The methods of the present invention do not depend on the two or more upa boxes being separated within the promoter nucleotide sequence by a particular number of contiguous nucleotides. Each of the upa boxes can be adjacent to each other or separated in the promoter nucleotide sequence by 2, 5, 10, 25, 50, 100, 125, 150, 200, 300, 500, 750, 1000, or more nucleotides.

In the methods disclosed herein, a promoter of gene that already comprises a upa box can be used. Such a gene, for example, is the native promoter of the R gene, Bs3 gene. The promoter of Bs3 is set forth in SEQ ID NO: 3. By "native promoter of an R gene" is intended to mean the promoter, or functional part thereof, of a naturally occurring plant R gene. With such a native promoter, the methods disclosed herein can be used to make pathogen-inducible promoter comprising one or more additional upa boxes. Such upa boxes can be inserted between the 5' end nucleotide and 3' end nucleotide of the native promoter or other promoter comprising a upa box, but preferably not within the upa box that is present in the native promoter or other promoter comprising a upa box. Alternatively or additionally, the additional upa boxes can be attached, ligated, or otherwise covalently bound to either the 5' and/or 3' ends of the native promoter or other promoter to produce a pathogen-inducible promoter comprising a contiguous nucleotide sequence. It is recognized that additional nucleotide sequences may be added when one or more upa boxes are inserted into, or attached, ligated, or covalently bound to a native promoter or other promoter comprising a upa box.

In one embodiment, the present invention provides a method for making a promoter that is inducible by two or more pathogens. The method involves producing a promoter comprising two or more upa boxes as described supra. Such a promoter comprises at least two different upa boxes, each of which binds to a TAL effector from a different plant pathogen. Promoters made by this method include, for example: a promoter comprising a upa box from the Bs3 promoter and a upa box from the Bs3-E promoter; a promoter comprising a upa box from the Bs3 promoter, a upa box from the Bs3-E promoter; and a upa box from the Xa27 promoter; and a promoter comprising a upa box from the Bs3 promoter and a upa box from the Xa27 promoter. Examples of these promoters have the nucleotide sequences set forth in SEQ ID NOS: 13-16. In a preferred embodiment, the methods of the invention are used to produce a pathogen-inducible promoter that is inducible by two or more different bacterial pathogens that are known to infect and cause economic damage to the same plant species, particularly a crop plant, more particularly rice, pepper, and a citrus species.

The methods of the present invention do not depend on the use of any particular upa boxes. Any upa box can be used in the methods disclosed herein. The methods for making a pathogen-inducible promoter of the present invention further comprise the use of upa boxes identified by additional methods of present invention that are disclosed herein below. Upa boxes of the present invention include but are not limited to $upa_{AvrBs3}$, $upa_{AvrBs3\Delta rep16}$, $upa_{AvrXa27}$, $upa_{PthXo1}$, $upa_{PthXo6}$ and $upa_{PthXo7}$. Nucleotide sequences comprising upa boxes include, but at not limited, to SEQ ID NOS: 17, 18, 20, 22, 24, 28-33, and 35-48.

The present invention provides methods for making an R gene, said method comprising producing a nucleic acid molecule comprising a promoter and an operably linked coding sequence for an R gene product. An R gene produced by the methods disclosed herein is capable of conferring upon a plant comprising said R gene increased resistance to infection by at least one plant pathogen. In a preferred embodiment, an R gene produced by the methods disclosed herein is capable of conferring upon a plant comprising said R gene increased resistance to infection by two or more plant pathogens, particularly bacterial plant pathogens, more particularly bacterial plant pathogens that produce at least one TAL effector. The methods of the present invention find use in making new R genes for use in producing crop plants and trees with enhanced resistance to one or more plant pathogens, thereby allowing for increased agricultural production while at the same time reducing the cost and negative environmental impact associated with the application of pesticides to crop plants and trees.

By "R gene product" is intended the gene product of a plant resistant gene referred to an R gene. For the present invention, such an R gene product is a protein that, when expressed in a plant, particularly at the site of infection of a pathogen, is capable of causing a hypersensitive response (HR) which is characterized by a programmed cell death response in the immediate vicinity of the pathogen. The methods of the present invention do not depend on the use of particular coding sequence for an R gene product. Any coding sequence of any R gene product can be employed in the methods disclosed herein. A preferred coding sequence is any nucleotide sequence comprising the coding sequence for the Bs3 protein or biologically active fragment or variant thereof. An example of such a Bs3 coding sequence is set forth in SEQ ID NO: 1. The nucleotide sequence of the Bs3 gene and coding sequence and the amino acid sequence of the Bs3 protein are available at GenBank as Accession No. EU078684, which is herein incorporated in its entirety by reference.

The methods of the present invention for making an R gene involve producing a nucleic acid molecule comprising a promoter and an operably linked coding sequence for an R gene product. Such a promoter comprises one or more upa boxes and can be produced the methods for making a pathogen-inducible promoter as disclosed herein. Such a promoter is capable of driving pathogen-inducible expression of the coding sequence for the R gene product. In one embodiment of the invention, the promoter comprises a native promoter of an R gene to which a upa box is added by the methods disclosed herein. Preferably, such a native promoter comprises at least one upa box that is different from the upa box that is added. More preferably, the promoter comprises two or more upa boxes that bind to different TAL effectors that from different plant pathogens that infect the same plant species.

The R genes of present invention find further use in methods for increasing the resistance of a plant to at least one plant pathogen. These methods of the invention comprise transforming a plant cell with an R gene produced by the methods of the present invention and regenerating a transformed plant from said transformed cell.

In one embodiment, the methods of the invention for making an R gene can be used to make an R genes specific to a particular bacterial pathogen when no naturally occurring R gene specific to the pathogen is known to exist. For example, most citrus species are susceptible to *Xanthomonas citri*, which is known to make at least three AvrBs3-like proteins. However, no R gene against *Xanthomonas citri* is known to exist in citrus species. Using the methods of the present invention, one or more upa boxes can be determined for a particular citrus plant species and a pathogen-inducible promoter comprising the upa box can be produced. Such upa boxes include, but are limited to, $UPT_{Apl1}$, $UPT_{Apl2}$, $UPT_{Apl3}$, $UPT_{PthB}$, $UPT_{PthA*}$, $UPT_{PthA*2}$, $UPT_{PthAw}$, $UPT_{PthA1}$, $UPT_{PthA2}$, $UPT_{PthA3}$, $UPT_{pB3.7}$, $UPT_{HssB3.0}$, $UPT_{PthA}$, and $UPT_{PthC}$, and the UPT boxes comprising the nucleotide sequences set forth in SEQ ID NOS: 35-48. A non-limiting example of a pathogen-inducible promoter of the present invention that comprises 14 UPT boxes for citrus canker pathogen TAL effectors comprises the nucleotide sequence set fort in SEQ ID NO: 34. The 14 UPT boxes in this promoter are $UPT_{Apl1}$, $UPT_{Apl2}$, $UPT_{Apl3}$, $UPT_{PthB}$, $UPT_{PthA*}$, $UPT_{PthA*2}$, $UPT_{PthAw}$, $UPT_{PthA1}$, $UPT_{PthA2}$, $UPT_{PthA3}$, $UPT_{pB3.7}$, $UPT_{HssB3.0}$, $UPT_{PthA}$, and $UPT_{PthC}$ and comprise the nucleotide sequences set forth in SEQ ID NOS: 35-48, respectively.

The methods of the present invention can be used to make a pathogen-inducible promoter that is inducible in a citrus plant species by one or more *Xanthomonas citri* strains and/or other citrus canker-causing *Xanthomonas* strains and that can be fused to a coding sequence for an R gene product. The coding sequence for any R gene product that is capable of causing a HR in the citrus plant species can be used. Such a coding sequence for any R gene product can originate from a native R gene of the citrus species wherein the R gene is specific to pathogen other than *Xanthomonas citri* or other citrus canker-causing *Xanthomonas* strains. Alternatively, the coding sequence for the R gene product can originate from R gene that is from a different plant species.

The methods of the present invention provide pathogen-inducible promoters and R genes comprising such pathogen-inducible promoters. In preferred embodiments of the invention, pathogen-inducible promoters and R genes comprising such pathogen-inducible promoters are inducible by two or more different plant pathogens, particularly bacterial plant pathogens. For the purposes of present different plant pathogens or different bacterial plant pathogens include different pathovars or strains within in the same species. For example, the rice pathogens, *Xanthomonas oryzae* pv. *oryzae* (Xoo) and *Xanthomonas oryzae* pv. *oryzicola* (Xoc) are considered different plant pathogens or different bacterial plant pathogens. Even different strains within a particular pathovar are different plant pathogens or different bacterial plant pathogens for the present invention, when such strains differ in their complements of TAL effectors.

The present invention additionally provides methods for identifying a upa box in the promoter of a gene from a plant. The methods involve exposing a plant, plant part, or plant cell to a TAL effector. The present invention does not depend a particular method exposing a plant, a plant part, or a plant cell. The exposing can comprise applying at least one bacterial cell to said plant, plant part, or plant cell, wherein said bacterial cell produces said TAL effector. Such a bacterial cell can be, for example, a plant pathogenic bacterial cell that expresses the TAL effector from its native genome. Alternatively, the TAL effector or an expression cassette suitable for the expression of an AvrBs3-like protein in a plant can presented or introduced on or into a plant by any know method including, for example, injection, addition to a cell culture medium, spraying, and infiltration. It is further recognized an expression cassette suitable for the expression of an AvrBs3-like protein in a plant can be part of a T-DNA within an *Agrobacterium* and that that plant can be exposed to the expression cassette by *Agrobacterium*-mediated delivery, which can involve, but does not depend on, infiltration of the *Agrobacterium* into a plant, a plant part, or a plant cell.

The methods for identifying a upa box in the promoter of a gene from a plant further involve, after exposing the plant, the plant part, or the plant cell to the TAL effector, identifying at least two genes in the plant, plant part, or plant cell, wherein the expression of the two or more genes are directly induced following exposure to said TAL effector. Preferably, at least three, four, five, or more genes are identified are directly induced following exposure to said TAL effector. A gene that is "directly induced" following the application of a TAL does not require any protein synthesis to occur for the induction of the gene, and protein synthesis can be blocked by the application of a protein synthesis inhibitor such as, for example, cycloheximide, and induction of the gene still occurs following exposure to the TAL effector. Typically, the protein synthesis inhibitor is added a few minutes before, but preferably at the same time as, the plant, the plant part, or the plant cell is first exposed to the TAL effector. It is recognized that the protein synthesis inhibitor can be added shortly after (e.g., 1-5 minutes) the plant, the plant part, or the plant cell is first exposed to the TAL effector to block effectively the expression of genes that require protein synthesis for their expression following exposure of the plant, the plant part, or the plant cell to the TAL effector.

The methods of the present invention do not depend on a particularly method identifying genes that display increased expression in the plant, the plant part, or the plant cell following exposure to the TAL. Any methods can be used including, but not limited to, differential display (Liang & Pardee (1992) *Science* 257:967-971; Sompayrac et al. (1995) *Nuc. Acids Res.* 23:4738-4739; Bartlett (2003) *Methods Mol. Biol.* 226: 217-224), serial analysis of gene expression (SAGE) (Velculescu et al. (1995) *Science* 270:484-487; Tuteja & Tuteja (2004) *Bioessays* 26:916-922), and analysis of DNA microarrays (DeRisi et al. (1997) *Science* 278:680-686; Schena et al. (1998) *Trends Biotechnol.* 1998; 16:217-218; Schulze & Downward (2001) *Nature Cell Biol.* 3:E190-E195). It is recognized that timing of when increased gene expression is detectable will vary depending on number factors including, for example, the particular host plant and TAL effector combination, environmental conditions, and exposure method. Typically for the methods of the present invention, the optimal timing for harvesting plant tissue for use in gene expression analysis is between 4 and 48 hours after exposure to the TAL effector, preferably between 12 and 36 hours, more preferably between about 18 and 30 hours, and most preferably at 24 hours after exposure to the TAL effector. It is further recognized that once genes are identified, the nucleotide sequences of the genes or parts thereof (i.e., promoter regions) can be obtained by standard methods such as, for example, cloning and sequencing. It is recognized that one or more genes may already be known that display increased expression in the plant, the plant part, or the plant cell following exposure to the TAL. In such a circumstance, the identifying step does not require any experimentation. The methods of the invention additionally involve obtaining the nucleotide sequences of the two or more genes, particularly the promoter regions or part thereof. Such nucleotide sequences can be obtained by standard sequence methods or from nucleotide sequence databases, if the gene sequence is already known.

The methods for identifying a upa box in the promoter of a gene from a plant further involve comparing the nucleotide sequences of the promoters of said at least two or more genes to identify at least one nucleotide sequence subsequence comprising at least one potential upa box. The methods additionally involve assaying at least one nucleotide molecule comprising said subsequence for upa-box activity and identifying a upa box when said subsequence comprises upa-box activity.

For example, the methods of the present invention can be used to identify upa boxes in any plant. Preferred plants include plants of economic importance and that are known to suffer damage from bacterial pathogens. Such preferred plants include, but are not limited to crop plants, fruit trees, timber species, and ornamental plants. In one embodiment of the invention, the methods for identifying a upa box are used to identify a upa box in rice. Several bacterial pathogens that infect rice plants are known to produce AvrBs3-like proteins (also known as TAL effectors). For example, strains of the rice pathogen *Xanthomonas oryzae* pv. *oryzae* are known to produce up to 19 AvrBs3-like proteins. For three of these AvrBs3-like proteins PthXo1, PthXo6, and PthXo7 (Yang et al. (2006) *Proc. Natl. Acad. Sci. USA* 103:10503-10508; Sugio et al. (2007) *Proc. Natl. Acad. Sci. USA* 104:10720-10725; Salzberg et al. (2008) *BMC Genomics* 9:204), corresponding host genes have been identified. Nucleotide and amino acid sequences for these three AvrBs3-like proteins are set forth in Accession Nos. YP001912775, AAS46025, ABB70183, YP001913452, ABB70129, and YP001911730; each of which is herein incorporated in its entirety by reference. In addition, rice genes that are induced by each of these AvrBs3-like proteins are also known. For PthXo1, the rice gene is Os8N3 (also know as Xa13) (Accession Nos. ABD78944 and ABD78943; each of which is herein incorporated in its entirety by reference). For PthXo6, the rice gene is OsTFX1 (Accession No. AK108319; herein incorporated in its entirety by reference). For PthXo7, the rice gene is OsTFIIA1γ (Accession No. CB097192; herein incorporated in its entirety by reference). Using the methods disclosed herein, a upa box that binds to each of these three AvrBs3-like proteins can be identified.

In the description herein of the present invention, reference is made to a upa box binding to a TAL effector and to "upa-box activity." Unless expressly stated otherwise or obvious from the context, such binding refers to binding that occurs between a upa box and a TAL effector, wherein such binding is capable of causing the expression of a polynucleotide molecule that is operably linked to a promoter comprising the upa box. Similarly, a upa box displays "upa-box activity" when, in the presence of an corresponding TAL effector, a nucleic acid molecule or promoter comprising the upa box directs in a plant, plant part, or plant cell the expression of a polynucleotide molecule that is operably linked to the nucleic acid molecule or promoter comprising the upa box. Such upa-box activity can be assayed, for example, by the transient expression assay as described herein below. Such a transient assay involves the co-delivery of both a gene encoding the TAL effector and a polynucleotide construct comprising a polynucleotide molecule operably linked to the nucleic acid molecule comprising the upa box. Such an assay is also described in U.S. Patent Application Publication No. 2009/0133158, and WO 2009/042753, and Römer et al. (2007) Science 318: 645-648.

The present invention additionally provides isolated nucleic acid molecules comprising at least one of the pathogen-inducible promoters that are made by the methods disclosed herein, at least one of the upa boxes of the present invention, and/or an R gene that is produced by the methods disclosed herein. The nucleic acid molecules of the invention include, but are not limited to, those comprising the nucleotide sequences set forth in SEQ ID NOS: 6, 7, 9, 11, 13-18, 20, 22, 24, and 28-48 and fragments and variants thereof that comprise upa-box activity. Such isolated nucleic acid molecules find use in producing plants, particularly crop plants, with enhanced resistance to one or more plant pathogens. The invention further provides expression cassettes, plants, plant parts, plant cells, seeds and non-human host cells comprising the nucleic acid molecules of the present invention.

The methods for increasing the resistance of a plant to at least one plant pathogen can involve one or R genes in addition to an R gene produced by the methods of the present invention. The additional R gene or genes can increase the resistance of a plant to a single plant pathogen or increase plant resistant to different plant pathogen. For example, a pepper plant comprising the Bs2 and/or Bs3 resistance genes can be transformed with an R gene of the present invention. The nucleotide sequences of the Bs2 and Bs3 have been previously disclosed. See, U.S. Pat. Nos. 6,262,343 and 6,762,285 and Accession No. EU078684; each of which is herein incorporated by reference.

Thus, the invention further provides methods for expressing a gene of interest in a plant, plant part, or plant cell. The methods involve operably linking a promoter of the present invention to a gene of interest so as to produce a polynucleotide construct. Such genes of interest will depend on the desired outcome and can comprise nucleotide sequences that encode proteins and/or RNAs of interest. The methods further involve transforming at least one plant cell with the polynucleotide construct. The methods can additionally involve regenerating the transformed plant cell into a transformed plant. The gene of interest is expressed when the promoter is induced after exposing the plant, plant part, or plant cell to a corresponding TAL effector.

By "gene of interest" is intended any nucleotide sequence that can be expressed when operable linked to a promoter. A gene of interest of the present invention may, but need not, encode a protein. Unless stated otherwise or readily apparent from the context, when a gene of interest of the present invention is said to be operably linked to a promoter of the invention, the gene of interest does not by itself comprise a functional promoter.

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Fragments and variants of the disclosed polynucleotides and proteins encoded thereby are also encompassed by the present invention. By "fragment" is intended a portion of the polynucleotide or a portion of the amino acid sequence and hence protein encoded thereby. Fragments of polynucleotides comprising coding sequences may encode protein fragments that retain biological activity of the native protein. Fragments of polynucleotide comprising promoter sequences retain biological activity of the full-length promoter, particularly upa-box activity. Alternatively, fragments of a polynucleotide that are useful as hybridization probes generally do not encode proteins that retain biological activity or do not retain promoter activity. Thus, fragments of a nucleotide sequence may range from at least about 20 nucleotides, about 50 nucleotides, about 100 nucleotides, and up to the full-length polynucleotide of the invention.

A fragment of a polynucleotide of the invention may encode a biologically active portion of a pathogen-inducible promoter, upa box or R gene or it may be a fragment that can be used as a hybridization probe or PCR primer using methods disclosed below. A biologically active portion of a pathogen-inducible promoter, upa box or the pathogen-inducible promoter of an R gene can be prepared by isolating a portion of one of the polynucleotides of the invention that comprises the promoter or upa-box and assessing upa-box activity as described herein. Polynucleotides that are fragments of a nucleotide sequence of the present invention comprise at least 9, 10, 11, 12, 13, 14, 15, 16, 17, 18, 19, 20, 21, 22, 23, 24, 25, 30, 35, 40, 45, 50, 75, 100, 125, 150, 175, 200, 250, 300, 350, 400, 450, 500, 550, 600, 650, 700, 800, 900, 1000, 1100, 1200, 1300, 1400, 1500, 2000, 2500, or 3000 contiguous nucleotides, or up to the number of nucleotides present in a full-length polynucleotide disclosed herein (for example, 1059, 1059, 166, 1557, 1070, 1107, 1059, 1104, 19, 15, 35, 18, an 48 nucleotides for SEQ ID NOS: 6, 7, 9, 11, 13-18, 20, 22, and 24, respectively).

"Variants" is intended to mean substantially similar sequences. For polynucleotides, a variant comprises a polynucleotide having deletions (i.e., truncations) at the 5' and/or 3' end; deletion and/or addition of one or more nucleotides at one or more internal sites in the native polynucleotide; and/or substitution of one or more nucleotides at one or more sites in the native polynucleotide. As used herein, a "native" polynucleotide or polypeptide comprises a naturally occurring nucleotide sequence or amino acid sequence, respectively. For polynucleotides that comprise coding sequences, conservative variants include those sequences that, because of the degeneracy of the genetic code, encode the amino acid sequence of one of the polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still comprise upa-box activity. Generally, variants of a particular polynucleotide or nucleic acid molecule of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters as described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion (so-called truncation) of one or more amino acids at the N-terminal and/or C-terminal end of the native protein; deletion and/or addition of one or more amino acids at one or more internal sites in the native protein; or substitution of one or more amino acids at one or more sites in the native protein. Variant proteins encompassed by the present invention are biologically active; that is they continue to possess the desired biological activity of the native protein. Such variants may result from, for example, genetic polymorphism or from human manipulation. Biologically active variants of a protein of the invention will have at least about 60%, 65%, 70%, 75%, 80%, 85%, 90%, 91%, 92%, 93%, 94%, 95%, 96%, 97%, 98%, 99% or more sequence identity to the amino acid sequence for the native protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

The proteins of the invention may be altered in various ways including amino acid substitutions, deletions, truncations, and insertions. Methods for such manipulations are generally known in the art. For example, amino acid sequence variants and fragments of the proteins can be prepared by mutations in the DNA. Methods for mutagenesis and polynucleotide alterations are well known in the art. See, for example, Kunkel (1985) *Proc. Natl. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass both naturally occurring proteins as well as variations and modified forms thereof. Such variants will continue to possess the desired biological activity. Obviously, the mutations that will be made in the DNA encoding the variant must not place the sequence out of reading frame and optimally will not create complementary regions that could produce secondary mRNA structure. See, EP Patent Application Publication No. 75,444.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays. That is, the activity can be evaluated by flavin-dependent monooxygenase activity assays. See, for example, Krueger et al. (2005). *Pharmacol. Ther.* 106, 357-387; herein incorporated by reference.

Variant polynucleotides and proteins also encompass sequences and proteins derived from a mutagenic and recombinogenic procedure such as DNA shuffling. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

The polynucleotides of the invention can be used to isolate corresponding sequences from other organisms, particularly other plants. In this manner, methods such as PCR, hybridization, and the like can be used to identify such sequences based on their sequence homology to the sequences set forth herein. Sequences isolated based on their sequence identity to the entire sequences set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99%, or greater sequence identity. Functions of orthologs are often highly conserved among species. Thus, isolated polynucleotides that have upa-box promoter activity and which hybridize under stringent conditions to at least one of the polynucleotides disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the polynucleotides of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N.Y.).

For example, an entire nucleic acid molecule of polynucleotide disclosed herein, or one or more portions thereof, may be used as a probe capable of specifically hybridizing to corresponding polynucleotide and messenger RNAs. To achieve specific hybridization under a variety of conditions, such probes include sequences that are unique among one or more of the polynucleotide sequences of the present invention and are optimally at least about 10 nucleotides in length, and most optimally at least about 20 nucleotides in length. Such probes may be used to amplify corresponding polynucleotides from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid*

*Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Plainview, N.Y.).

It is recognized that the polynucleotide molecules of the present invention encompass polynucleotide molecules comprising a nucleotide sequence that is sufficiently identical to one of the nucleotide sequences set forth in SEQ ID NOS: 6, 7, 9, 11, 13-18, 20, 22, or 24. The term "sufficiently identical" is used herein to refer to a first amino acid or nucleotide sequence that contains a sufficient or minimum number of identical or equivalent nucleotides to a second nucleotide sequence such that the first and second nucleotide sequences have a common structural domain and/or common functional activity. For example, nucleotide sequences that contain a common structural domain having at least about 45%, 55%, or 65% identity, preferably 75% identity, more preferably 85%, 90%, 95%, 96%, 97%, 98% or 99% identity are defined herein as sufficiently identical.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. The percent identity between two sequences can be determined using techniques similar to those described below, with or without allowing gaps. In calculating percent identity, typically exact matches are counted.

The determination of percent identity between two sequences can be accomplished using a mathematical algorithm. A preferred, nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci.* USA 90:5873-5877. Such an algorithm is incorporated into the NBLAST and XBLAST programs of Altschul et al. (1990) *J. Mol. Biol.* 215:403. BLAST nucleotide searches can be performed with the NBLAST program, score=100, wordlength=12, to obtain nucleotide sequences homologous to the polynucleotide molecules of the invention. BLAST protein searches can be performed with the XBLAST program, score=50, wordlength=3, to obtain amino acid sequences homologous to protein molecules of the invention. To obtain gapped alignments for comparison purposes, Gapped BLAST can be utilized as described in Altschul et al. (1997) *Nucleic Acids Res.* 25:3389. Alternatively, PSI-Blast can be used to perform an iterated search that detects distant relationships between molecules. See Altschul et al. (1997) *supra*. When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller (1988) CABIOS 4:11-17. Such an algorithm is incorporated into the ALIGN program (version 2.0), which is part of the GCG sequence alignment software package. When utilizing the ALIGN program for comparing amino acid sequences, a PAM120 weight residue table, a gap length penalty of 12, and a gap penalty of 4 can be used. Alignment may also be performed manually by inspection.

Unless otherwise stated, sequence identity/similarity values provided herein refer to the value obtained using the full-length sequences of the invention and using multiple alignment by mean of the algorithm Clustal W (Nucleic Acid Research, 22(22):4673-4680, 1994) using the program AlignX included in the software package Vector NTI Suite Version 7 (InforMax, Inc., Bethesda, MD, USA) using the default parameters; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by CLUSTALW (Version 1.83) using default parameters (available at the European Bioinformatics Institute website which is available on the World Wide Web at ebi.ac.uk/Tools/clustalw/index.html).

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures, and the like.

The pathogen-inducible promoters, upa boxes and R genes of the present invention can be provided in expression cassettes for expression in the plant or other organism or non-human host cell of interest. The cassette will include 5' and 3' regulatory sequences operably linked to polynucleotide to be expressed. "Operably linked" is intended to mean a functional linkage between two or more elements. For example, an operable linkage between a polynucleotide or gene of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the polynucleotide to be under the transcriptional regulation of the regulatory regions. The expression cassette may additionally contain selectable marker genes.

The expression cassette will include in the 5'-3' direction of transcription, a transcriptional and translational initiation region (i.e., a promoter), polynucleotide to be expressed, and a transcriptional and translational termination region (i.e., termination region) functional in plants or other organism or non-human host cell. The regulatory regions (i.e., promoters, transcriptional regulatory regions, and translational termination regions) and/or the polynucleotide to be expressed may be native/analogous to the host cell or to each other. Alternatively, any of the regulatory regions and/or the polynucleotide to be expressed may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide. As used herein, a chimeric gene comprises a coding sequence operably linked to a transcription initiation region that is heterologous to the coding sequence.

The termination region may be native with the transcriptional initiation region, may be native with the operably linked polynucleotide of interest, may be native with the plant host, or may be derived from another source (i.e., foreign or heterologous) to the promoter, the polynucleotide of interest, the plant host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Unless stated otherwise or obvious from the context, a promoter of the present invention comprises a nucleotide sequence comprising at least one upa box and is capable of directing the expression of an operably linked polynucleotide in a plant, a plant part, and/or a plant cell. Preferably, a promoter of the present is invention is pathogen-inducible. More preferably, the promoter is inducible by a bacterial pathogen. Even more preferably, the promoter is inducible by a bacterial pathogen that produces a TAL effector. Most preferably, the promoter is inducible by a bacterial pathogen that produces a TAL effector that specifically binds to the upa box of the promoter.

Where appropriate, the polynucleotides may be optimized for increased expression in the transformed plant. That is, the polynucleotides can be synthesized using plant-preferred codons for improved expression. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Natl. Acad. Sci. USA* 86:6126-6130); potyvirus leaders, for example, TEV leader (Tobacco Etch Virus) (Gallie et al. (1995) *Gene* 165(2):233-238), MDMV leader (Maize Dwarf Mosaic Virus) (*Virology* 154:9-20), and human immunoglobulin heavy-chain binding protein (BiP) (Macejak et al. (1991) *Nature* 353:90-94); untranslated leader from the coat protein mRNA of alfalfa mosaic virus (AMV RNA 4) (Jobling et al. (1987) *Nature* 325:622-625); tobacco mosaic virus leader (TMV) (Gallie et al. (1989) in *Molecular Biology of RNA*, ed. Cech (Liss, New York), pp. 237-256); and maize chlorotic mottle virus leader (MCMV) (Lommel et al. (1991) *Virology* 81:382-385). See also, Della-Cioppa et al. (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su et al. (2004) *Biotechnol Bioeng* 85:610-9 and Fetter et al. (2004) *Plant Cell* 16:215-28), cyan florescent protein (CYP) (Bolte et al. (2004) *J. Cell Science* 117:943-54 and Kato et al. (2002) *Plant Physiol* 129:913-42), and yellow florescent protein (PhiYFP™ from Evrogen, see, Bolte et al. (2004) *J. Cell Science* 117:943-54). For additional selectable markers, see generally, Yarranton (1992) *Curr. Opin. Biotech.* 3:506-511; Christopherson et al. (1992) *Proc. Natl. Acad. Sci. USA* 89:6314-6318; Yao et al. (1992) *Cell* 71:63-72; Reznikoff (1992) *Mol. Microbiol.* 6:2419-2422; Barkley et al. (1980) in *The Operon*, pp. 177-220; Hu et al. (1987) *Cell* 48:555-566; Brown et al. (1987) *Cell* 49:603-612; Figge et al. (1988) *Cell* 52:713-722; Deuschle et al. (1989) *Proc. Natl. Acad. USA* 86:5400-5404; Fuerst et al. (1989) *Proc. Natl. Acad. Sci. USA* 86:2549-2553; Deuschle et al. (1990) *Science* 248:480-483; Gossen (1993) Ph.D. Thesis, University of Heidelberg; Reines et al. (1993) *Proc. Natl. Acad. Sci. USA* 90:1917-1921; Labow et al. (1990) *Mol. Cell. Biol.* 10:3343-3356; Zambretti et al. (1992) *Proc. Natl. Acad. Sci. USA* 89:3952-3956; Baim et al. (1991) *Proc. Natl. Acad. Sci. USA* 88:5072-5076; Wyborski et al. (1991) *Nucleic Acids Res.* 19:4647-4653; Hillenand-Wissman (1989) *Topics Mol. Struc. Biol.* 10:143-162; Degenkolb et al. (1991) *Antimicrob. Agents Chemother.* 35:1591-1595; Kleinschnidt et al. (1988) *Biochemistry* 27:1094-1104; Bonin (1993) Ph.D. Thesis, University of Heidelberg; Gossen et al. (1992) *Proc. Natl. Acad. Sci. USA* 89:5547-5551; Oliva et al. (1992) *Antimicrob. Agents Chemother.* 36:913-919; Hlavka et al. (1985) *Handbook of Experimental Pharmacology*, Vol. 78 (Springer-Verlag, Berlin); Gill et al. (1988) *Nature* 334:721-724. Such disclosures are herein incorporated by reference.

The above list of selectable marker genes is not meant to be limiting. Any selectable marker gene can be used in the present invention.

Numerous plant transformation vectors and methods for transforming plants are available. See, for example, An, G. et al. (1986) *Plant Pysiol.*, 81:301-305; Fry, J., et al. (1987) *Plant Cell Rep.* 6:321-325; Block, M. (1988) *Theor. Appl Genet.* 76:767-774; Hinchee, et al. (1990) *Stadler. Genet. Symp.* 203212.203-212; Cousins, et al. (1991) *Aust. J. Plant*

*Physiol.* 18:481-494; Chee, P. P. and Slightom, J. L. (1992) *Gene.* 118:255-260; Christou, et al. (1992) *Trends. Biotechnol.* 10:239-246; D'Halluin, et al. (1992) Bio/Technol. 10:309-314; Dhir, et al. (1992) *Plant Physiol.* 99:81-88; Casas et al. (1993) *Proc. Nat. Acad Sci. USA* 90:11212-11216; Christou, P. (1993) *In Vitro Cell. Dev. Biol.-Plant;* 29P:119-124; Davies, et al. (1993) *Plant Cell Rep.* 12:180-183; Dong, J. A. and Mchughen, A. (1993) *Plant Sci.* 91:139-148; Franklin, C. I. and Trieu, T. N. (1993) *Plant. Physiol.* 102:167; Golovkin, et al. (1993) *Plant Sci.* 90:41-52; *Guo Chin Sci. Bull.* 38:2072-2078; Asano, et al. (1994) *Plant Cell Rep.* 13; Ayeres N. M. and Park, W. D. (1994) *Crit. Rev. Plant. Sci.* 13:219-239; Barcelo, et al. (1994) *Plant. J.* 5:583-592; Becker, et al. (1994) *Plant. J.* 5:299-307; Borkowska et al. (1994) *Acta. Physiol Plant.* 16:225-230; Christou, P. (1994) *Agro. Food. Ind. Hi Tech.* 5: 17-27; Eapen et al. (1994) *Plant Cell Rep.* 13:582-586; Hartman, et al. (1994) *Bio-Technology* 12: 919923; Ritala, et al. (1994) *Plant. Mol. Biol.* 24:317-325; and Wan, Y. C. and Lemaux, P. G. (1994) *Plant Physiol.* 104:3748.

The methods of the invention involve introducing a polynucleotide construct into a plant. By "introducing" is intended presenting to the plant the polynucleotide construct in such a manner that the construct gains access to the interior of a cell of the plant. The methods of the invention do not depend on a particular method for introducing a polynucleotide construct to a plant, only that the polynucleotide construct gains access to the interior of at least one cell of the plant. Methods for introducing polynucleotide constructs into plants are known in the art including, but not limited to, stable transformation methods, transient transformation methods, and virus-mediated methods.

By "stable transformation" is intended that the polynucleotide construct introduced into a plant integrates into the genome of the plant and is capable of being inherited by progeny thereof. By "transient transformation" is intended that a polynucleotide construct introduced into a plant does not integrate into the genome of the plant.

For the transformation of plants and plant cells, the nucleotide sequences of the invention are inserted using standard techniques into any vector known in the art that is suitable for expression of the nucleotide sequences in a plant or plant cell. The selection of the vector depends on the preferred transformation technique and the target plant species to be transformed.

Methodologies for constructing plant expression cassettes and introducing foreign nucleic acids into plants are generally known in the art and have been previously described. For example, foreign DNA can be introduced into plants, using tumor-inducing (Ti) plasmid vectors. Other methods utilized for foreign DNA delivery involve the use of PEG mediated protoplast transformation, electroporation, microinjection whiskers, and biolistics or microprojectile bombardment for direct DNA uptake. Such methods are known in the art. (U.S. Pat. No. 5,405,765 to Vasil et al.; Bilang et al. (1991) *Gene* 100: 247-250; Scheid et al., (1991) *Mol. Gen. Genet.,* 228: 104-112; Guerche et al., (1987) *Plant Science* 52: 111-116; Neuhause et al., (1987) *Theor. Appl Genet.* 75: 30-36; Klein et al., (1987) *Nature* 327: 70-73; Howell et al., (1980) *Science* 208:1265; Horsch et al., (1985) *Science* 227: 1229-1231; DeBlock et al., (1989) *Plant Physiology* 91: 694-701*; Methods for Plant Molecular Biology* (Weissbach and Weissbach, eds.) Academic Press, Inc. (1988) and *Methods in Plant Molecular Biology* (Schuler and Zielinski, eds.) Academic Press, Inc. (1989). The method of transformation depends upon the plant cell to be transformed, stability of vectors used, expression level of gene products and other parameters.

Other suitable methods of introducing nucleotide sequences into plant cells and subsequent insertion into the plant genome include microinjection as Crossway et al. (1986) *Biotechniques* 4:320-334, electroporation as described by Riggs et al. (1986) *Proc. Natl. Acad. Sci. USA* 83:5602-5606, *Agrobacterium*-mediated transformation as described by Townsend et al., U.S. Pat. No. 5,563,055, Zhao et al., U.S. Pat. No. 5,981,840, direct gene transfer as described by Paszkowski et al. (1984) *EMBO J.* 3:2717-2722, and ballistic particle acceleration as described in, for example, Sanford et al., U.S. Pat. No. 4,945,050; Tomes et al., U.S. Pat. No. 5,879,918; Tomes et al., U.S. Pat. No. 5,886, 244; Bidney et al., U.S. Pat. No. 5,932,782; Tomes et al. (1995) "Direct DNA Transfer into Intact Plant Cells via Microprojectile Bombardment," in *Plant Cell, Tissue, and Organ Culture: Fundamental Methods*, ed. Gamborg and Phillips (Springer-Verlag, Berlin); McCabe et al. (1988) *Bio-technology* 6:923-926); and Lec1 transformation (WO 00/28058). Also see, Weissinger et al. (1988) *Ann. Rev. Genet.* 22:421-477; Sanford et al. (1987) *Particulate Science and Technology* 5:27-37 (onion); Christou et al. (1988) *Plant Physiol.* 87:671-674 (soybean); McCabe et al. (1988) *Bio/Technology* 6:923-926 (soybean); Finer and McMullen (1991) *In Vitro Cell Dev. Biol.* 27P:175-182 (soybean); Singh et al. (1998) *Theor. Appl. Genet.* 96:319-324 (soybean); Datta et al. (1990) *Biotechnology* 8:736-740 (rice); Klein et al. (1988) *Proc. Natl. Acad. Sci. USA* 85:4305-4309 (maize); Klein et al. (1988) *Biotechnology* 6:559-563 (maize); Tomes, U.S. Pat. No. 5,240,855; Buising et al., U.S. Pat. Nos. 5,322, 783 and 5,324,646; Tomes et al. (1995) "Direct DNA Transfer into Intact Plant Cells via Microprojectile Bombardment," in *Plant Cell, Tissue, and Organ Culture: Fundamental Methods*, ed. Gamborg (Springer-Verlag, Berlin) (maize); Klein et al. (1988) *Plant Physiol.* 91:440-444 (maize); Fromm et al. (1990) *Biotechnology* 8:833-839 (maize); Hooykaas-Van Slogteren et al. (1984) *Nature (London)* 311:763-764; Bowen et al., U.S. Pat. No. 5,736,369 (cereals); Bytebier et al. (1987) *Proc. Natl. Acad. Sci. USA* 84:5345-5349 (Liliaceae); De Wet et al. (1985) in *The Experimental Manipulation of Ovule Tissues*, ed. Chapman et al. (Longman, New York), pp. 197-209 (pollen); Kaeppler et al. (1990) *Plant Cell Reports* 9:415-418 and Kaeppler et al. (1992) *Theor. Appl. Genet.* 84:560-566 (whisker-mediated transformation); D'Halluin et al. (1992) *Plant Cell* 4:1495-1505 (electroporation); Li et al. (1993) *Plant Cell Reports* 12:250-255 and Christou and Ford (1995) *Annals of Botany* 75:407-413 (rice); Osjoda et al. (1996) *Nature Biotechnology* 14:745-750 (maize via *Agrobacterium tumefaciens*); all of which are herein incorporated by reference.

The polynucleotides of the invention may be introduced into plants by contacting plants with a virus or viral nucleic acids. Generally, such methods involve incorporating a polynucleotide construct of the invention within a viral DNA or RNA molecule. It is recognized that the a protein of the invention may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotide constructs into plants and expressing a protein encoded therein, involving viral DNA or RNA molecules, are known in the art. See, for example, U.S. Pat. Nos. 5,889,191, 5,889,190, 5,866, 785, 5,589,367 and 5,316,931; herein incorporated by reference.

In specific embodiments, the nucleotide sequences of the invention can be provided to a plant using a variety of transient transformation methods. Such transient transformation methods include, but are not limited to, the introduction of the a protein or variants and fragments thereof directly into the plant or the introduction of a transcript into the plant. Such methods include, for example, microinjection or particle bombardment. See, for example, Crossway et al. (1986) *Mol Gen. Genet.* 202:179-185; Nomura et al. (1986) *Plant Sci.* 44:53-58; Hepler et al. (1994) *Proc. Natl. Acad. Sci.* 91: 2176-2180 and Hush et al. (1994) *The Journal of Cell Science* 107:775-784, all of which are herein incorporated by reference. Alternatively, the polynucleotide can be transiently transformed into the plant using techniques known in the art. Such techniques include viral vector system and *Agrobacterium tumefaciens*-mediated transient expression as described below.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide construct of the invention, for example, an expression cassette of the invention, stably incorporated into their genome.

The present invention may be used for transformation of any plant species, including, but not limited to, monocots and dicots. Examples of plant species of interest include, but are not limited to, peppers (*Capsicum* spp; e.g., *Capsicum annuum, C. baccatum, C. chinense, C. frutescens, C. pubescens*, and the like), tomatoes (*Lycopersicon esculentum*), tobacco (*Nicotiana tabacum*), eggplant (*Solanum melongena*), petunia (*Petunia* spp., e.g., *Petunia×hybrida* or *Petunia hybrida*), corn or maize (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers. *Citrus* spp. include, but are not limited to, cultivated *citrus* species, such as, for example, orange, lemon, meyer lemon, lime, key lime, Australian limes, grapefruit, mandarin orange, clementine, tangelo, tangerine, kumquat, pomelo, ugli, blood orange, and bitter orange.

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruits, roots, root tips, anthers, and the like. Progeny, variants, and mutants of the regenerated plants are also included within the scope of the invention, provided that these parts comprise the introduced polynucleotides.

The invention is drawn to compositions and methods for increasing resistance to plant disease. By "disease resistance" is intended that the plants avoid the disease symptoms that are the outcome of plant-pathogen interactions. That is, pathogens are prevented from causing plant diseases and the associated disease symptoms, or alternatively, the disease symptoms caused by the pathogen is minimized or lessened.

Pathogens of the invention include, but are not limited to, viruses or viroids, bacteria, insects, nematodes, fungi, and the like. Viruses include any plant virus, for example, tobacco or cucumber mosaic virus, ringspot virus, necrosis virus, maize dwarf mosaic virus, etc. Fungal pathogens, include but are not limited to, *Colletotrichum graminocola, Diplodia maydis, Fusarium graminearum*, and *Fusarium verticillioides*. Specific pathogens for the major crops include: Soybeans: *Phytophthora megasperma* fsp. *glycinea, Macrophomina phaseolina, Rhizoctonia solani, Sclerotinia sclerotiorum, Fusarium oxysporum, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassiicola, Septoria glycines, Phyllosticta sojicola, Alternaria alternate, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines Fusarium solani*; Canola: *Albugo candida, Alternaria brassicae, Leptosphaeria maculans, Rhizoctonia solani, Sclerotinia sclerotiorum, Mycosphaerella brassicicola, Pythium ultimum, Peronospora parasitica, Fusarium roseum, Alternaria alternata*; Alfalfa: *Clavibacter michiganese* subsp. *insidiosum, Pythium ultimum, Pythium irregulare, Pythium splendens, Pythium debaryanum, Pythium aphanidermatum, Phytophthora megasperma, Peronospora trifoliorum, Phoma medicaginis* var. *medicaginis, Cercospora medicaginis, Pseudopeziza medicaginis, Leptotrochila medicaginis, Fusarium oxysporum, Verticillium albo-atrum, Xanthomonas campestris* p.v. *alfalfae, Aphanomyces euteiches, Stemphylium herbarum, Stemphylium alfalfae, Colletotrichum trifolii, Leptosphaerulina briosiana, Uromyces striatus, Sclerotinia trifoliorum, Stagonospora meliloti, Stemphylium botryosum, Leptotrichila medicaginis*; Wheat: *Pseudomonas syringae* p.v. *atrofaciens, Urocystis agropyri, Xanthomonas campestris* p.v. *translucens, Pseudomonas syringae* p.v. *syringae, Alternaria alternata, Cladosporium herbarum, Fusarium graminearum, Fusarium avenaceum, Fusarium culmorum, Ustilago tritici, Ascochyta tritici, Cephalosporium gramineum, Collotetrichum graminicola, Erysiphe graminis* f.sp. *tritici, Puccinia graminis* f.sp. *tritici, Puccinia recondite* f.sp. *tritici, Puccinia striiformis, Pyrenophora tritici-repentis, Septoria nodorum, Septoria tritici, Septoria avenae, Pseudocercosporella herpotrichoides, Rhizoctonia solani, Rhizoctonia cerealis, Gaeumannomyces graminis* var. *tritici, Pythium aphanidermatum, Pythium arrhenomanes, Pythium ultimum, Bipolaris sorokiniana*, Barley Yellow Dwarf Virus, Brome Mosaic Virus, Soil Borne Wheat Mosaic Virus, Wheat Streak Mosaic Virus, Wheat Spindle Streak Virus, American Wheat Striate Virus, *Claviceps purpurea, Tilletia tritici, Tilletia laevis, Ustilago tritici, Tilletia indica, Rhizoctonia solani, Pythium arrhenomannes, Pythium gramicola, Pythium aphanidermatum*, High Plains Virus, European wheat striate virus; Sunflower: *Plasmopora halstedii, Sclerotinia sclerotiorum*, Aster Yellows, *Septoria helianthi, Phomopsis helianthi, Alternaria helianthi, Alternaria zinniae, Botrytis cinerea, Phoma macdonaldii, Macrophomina phaseolina, Erysiphe cichoracearum, Rhizopus oryzae, Rhizopus arrhizus, Rhizopus stolonifer, Puccinia helianthi, Verticillium dahliae, Erwinia carotovorum* pv. *carotovora, Cephalosporium acremonium, Phytophthora cryptogea, Albugo tragopogonis*; Corn: *Colletotrichum graminicola, Fusarium moniliforme* var. *subglutinans, Erwinia stewartii, F. verticillioides, Gibberella zeae (Fusarium graminearum), Stenocarpella maydi (Diplodia maydis), Pythium irregulare, Pythium debaryanum, Pythium graminicola, Pythium splendens, Pythium ultimum, Pythium aphanidermatum, Aspergillus flavus, Bipolaris maydis* O, T (*Cochliobolus heterostrophus*), *Helminthosporium carbonum* I, II & III (*Cochliobolus carbonum*), *Exserohilum turcicum* I, II & III, *Helminthosporium pedicellatum, Physoderma maydis, Phyllosticta maydis, Kabatiella maydis, Cercospora sorghi, Ustilago maydis, Puccinia sorghi, Puccinia polysora, Macrophomina phaseolina, Penicillium oxalicum, Nigrospora oryzae, Cladosporium herbarum, Curvularia lunata, Curvularia inaequalis, Curvularia pallescens, Clavibacter michiganense* subsp. *nebraskense, Trichoderma viride*, Maize Dwarf Mosaic Virus A & B, Wheat Streak Mosaic Virus, Maize Chlorotic Dwarf Virus, *Claviceps sorghi, Pseudonomas avenae, Erwinia chrysanthemi* pv. *zea, Erwinia carotovora*, Corn stunt *spiroplasma, Diplodia macrospora, Sclerophthora macrospora, Peronosclerospora sorghi, Peronosclerospora philippinensis, Peronosclerospora maydis, Peronosclerospora sacchari, Sphacelotheca reiliana, Physopella zeae, Cephalosporium maydis, Cephalosporium acremonium*, Maize Chlorotic Mottle Virus, High Plains Virus, Maize Mosaic Virus, Maize Rayado Fino Virus, Maize Streak Virus, Maize Stripe Virus, Maize Rough Dwarf Virus; Sorghum: *Exserohilum turcicum, C. sublineolum, Cercospora sorghi, Gloeocercospora sorghi, Ascochyta sorghina, Pseudomonas syringae* p.v. *syringae, Xanthomonas campestris* p.v. *holcicola, Pseudomonas andropogonis, Puccinia purpurea, Macrophomina phaseolina, Perconia circinate, Fusarium moniliforme, Alternaria alternate, Bipolaris sorghicola, Helminthosporium sorghicola, Curvularia lunata, Phoma insidiosa, Pseudomonas avenae (Pseudomonas alboprecipitans), Ramulispora sorghi, Ramulispora sorghicola, Phyllachara sacchari, Sporisorium reilianum (Sphacelotheca reiliana), Sphacelotheca cruenta, Sporisorium sorghi*, Sugarcane mosaic H, Maize Dwarf Mosaic Virus A & B, *Claviceps sorghi, Rhizoctonia solani, Acremonium strictum, Sclerophthona macrospora, Peronosclerospora sorghi, Peronosclerospora philippinensis, Sclerospora graminicola, Fusarium graminearum, Fusarium oxysporum, Pythium arrhenomanes, Pythium graminicola*, etc.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Various changes in phenotype are of interest including modifying the fatty acid composition in a plant, altering the amino acid content of a plant, altering a plant's pathogen defense mechanism, and the like. These results can be achieved by providing expression of heterologous products or increased expression of endogenous products in plants.

Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest include, for example, those genes involved in information, such as zinc fingers, those involved in communication, such as kinases, and those involved in housekeeping, such as heat shock proteins. More specific categories of transgenes, for example, include genes encoding important traits for agronomics, insect resistance, disease resistance, herbicide resistance, sterility, grain characteristics, and commercial products. Genes of interest include, generally, those involved in oil, starch, carbohydrate, or nutrient metabolism as well as those. In addition, genes of interest include genes encoding enzymes and other proteins from plants and other sources including prokaryotes and other eukaryotes.

The following examples are offered by way of illustration and not by way of limitation.

EXAMPLE 1

The Functionality of the upa$_{AvrBs3}$ Box does not Depend on its Position but Depends on its Orientation In order to test the functionality of the Bs3 promoter derivatives, a HR-based reporter assay was used. This assay, which is referred to herein as the "argo-infiltration assay," is based on the fact that *Agrobacterium*-mediated delivery of a T-DNA construct ("agroinfiltration") containing the Bs3 gene (Bs3 promoter+Bs3 coding sequence) triggers an HR in *Nicotiana benthamiana* if a T-DNA with a 35S Cauliflower mosaic virus-driven avrBs3 gene is co-delivered. In this assay, AvrBs3 will be expressed and activates the Bs3 promoter or derivatives thereof if they are compatible. In planta expression of the Bs3 protein triggers cell death. Thus, in the above described assay, the AvrBs3-inducibility of Bs3 promoter derivatives can be determined based on the presence or absence of an HR.

We first introduced point mutations into a sequence comprising the upa$_{AvrBs3}$ box (SEQ ID NO: 26: GCCTGAC-CAATTTTATTATATAAACCTAACCATCCTC; located 102 by 5' of the Bs3 ATG) of the Bs3 promoter and showed by the HR reporter assay, that some of these Bs3 promoter mutants did no longer trigger an HR when being agro-infiltrated together with a constitutively expressed avrBs3 gene. We now used one Bs3 promoter mutant derivative (referred to a "Bs3 $upa_{mut}$") that no longer triggers an AvrBs3-inducible HR (FIG. 1) for further studies (Bs3 $upa_{mut}$ sequence, SEQ ID NO: 27: GCCTGACCAATTTTATAATATAAACCTAACCATCCTC; mutated residue is underlined). The upaAvrBs3 box was inserted 294 and 424 by upstream (5') of the ATG inserted in the non-functional Bs3 $upa_{mut}$ promoter. Both promoter constructs (Bs3 $upa_{294}$ and Bs3 $upa_{424}$) were tested via the agro-infiltration assay described and were found to functional like the Bs3 wild-type promoter (FIG. 1). Thus, these results demonstrate that the upa$_{AvrBs3}$ box can be moved to other locations within the Bs3 promoter without losing its biological activity (i.e., upa box activity).

The upa$_{AvrBs3}$ box was also inserted in inverse orientation into the non-functional Bs3 upa$_{mut}$ promoter. However, this construct did not result in HR in the agro-infiltration assay. This result indicates that the orientation of the upa$_{AvrBs3}$ box is not flexible (data not shown).

EXAMPLE 2

Functionality of the upa$_{AvrBs3}$ Box is not Restricted to the Bs3 Promoter

The promoter of the tomato R gene Bs4 is expressed constitutively, but at very low levels (Schornack et al. (2005) *Mol. Plant Microbe Interact.* 18:1215-1225). When the Bs3 coding region was placed under the transcriptional control of the Bs4 promoter, this construct did not give HR in the agro-infiltration assay described in Example 1, irrespective of whether this construct is expressed with or without AvrBs3 (FIG. 1). The upa$_{AvrBs3}$ box and a mutated upa$_{AvrBs3}$ box (from the Bs3 upa$_{mut}$ promoter, see FIG. 1) were inserted 35 by 5' of the predicted TATA-Box of the Bs4 promoter. The construct comprising the Bs4 promoter with the upaAvrBs3 Box (Bs4 upa; SEQ ID NO: 9) showed an HR after being agro-infiltrated with a constitutively expressed avrBs3 gene (FIG. 1). By contrast a construct comprising a Bs4 promoter with a mutated upa$_{AvrBs3}$ box (Bs4 upa$_{mut}$; SEQ ID NO: 10) did not trigger an AvrBs3-dependent HR (FIG. 1). Thus, the upa$_{AvrBs3}$ box not only displays its biological activity (i.e., upa box activity) in the context of the pepper Bs3 promoter but also displays its biological activity in the context of the tomato Bs4 promoter. Thus, the function or biological activity of the upa$_{AvrBs3}$ box seems is not dependent on being located within one particular promoter.

EXAMPLE 3

Figure 2:
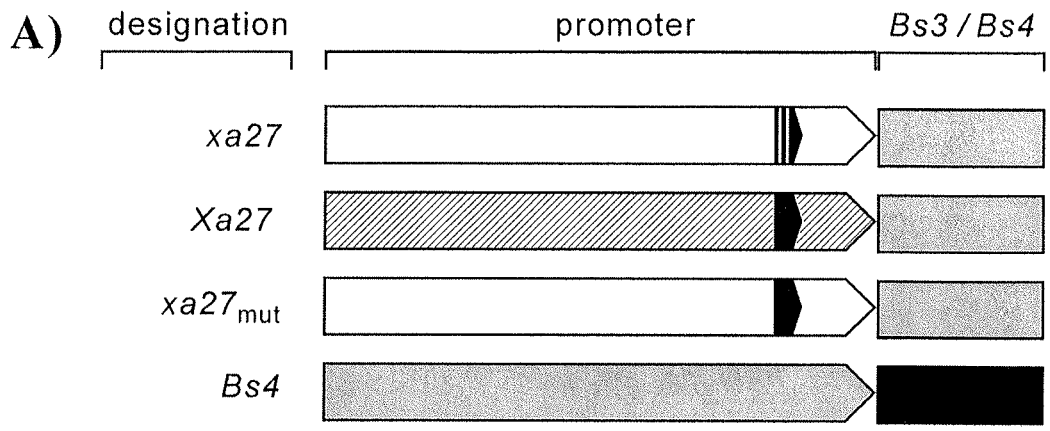
FIG. 2A. Schematic representation of the constructs that were used to study the promoter polymorphisms between the Xa27 and xa27 promoters and the functional relevance of these polymorphisms. White, hatched and gray boxes represent the xa27, Xa27, and Bs4 promoters, respectively. Small black boxes represent the upa$_{AvrXa27}$ box. Two nucleotide polymorphisms between the upa box of the xa27 promoter (not induced by AvrXa27) and the Xa27 promoter (induced by AvrXa27) are represented by two white lines. The xa27 and Xa27 promoters show in total 15 polymorhisms in a region of about 1 kb and are therefore displayed in different colors. The gray and black rectangles represent the coding regions of the pepper Bs3 and tomato Bs4 genes.
FIG. 2B. Functional analysis of polymorphisms between the Xa27 and xa27 promoter. The depicted promoter derivatives were delivered together with a 35S-driven avrXa27 gene into *Nicotiana benthamiana* leaves via *Agrobacterium tumefaciens* (OD600=0.8). Dashed lines mark the inoculated areas. Four days after infiltration, the leaves were cleared to visualize the HR (dark areas). Dark areas (marked with an asterisk [*]) represent functional promoters.
Figure 2:
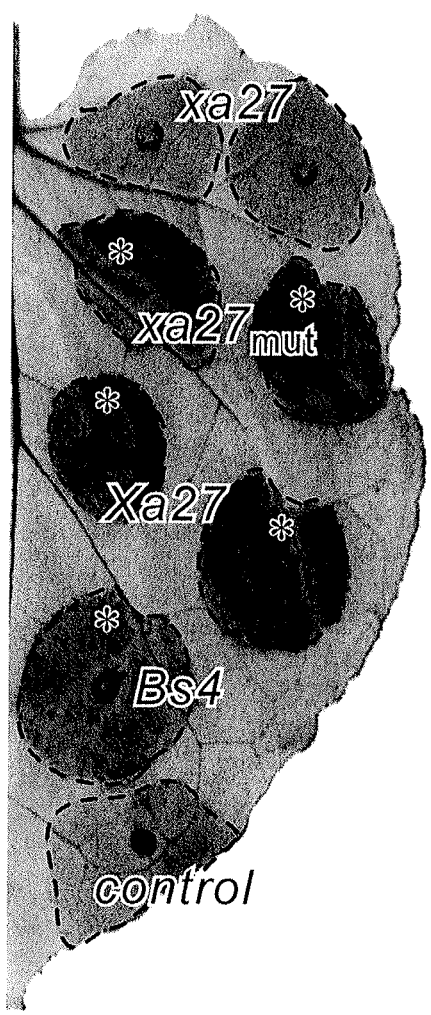

AvrXa27 and the Xa27 Promoter can Functionally Replace AvrBs3 and the Bs3 Promoter Constructs were made to test whether the combination of AvrXa27 from *Xanthomonas oryzae* pv. *oryzae* (Xoo) and the rice Xa27 promoter could functionally replace the *Xanthomonas campestris* pv. *vesicatoria* (Xcv) AvrBs3 protein and the matching pepper Bs3 promoter. The rice Xa27 promoter (Xa27$_{PROM}$; AvrXa27-inducible; SEQ ID NO: 11) and the allelic xa27 promoter (xa27$_{PROM}$; not AvrXa27 inducible; SEQ ID NO: 12) in front of the Bs3 coding region (Bs3$_{CDS}$; SEQ ID NO: 1) yielding two promoter constructs referred to Xa27$_{PROM}$-Bs3$_{CDS}$ and xa27$_{PROM}$-Bs3$_{CDS}$, respectively. Upon *Agrobacterium*-mediated delivery in the agro-infiltration assay, only Xa27$_{PROM}$-Bs3$_{CDS}$ but not the xa27$_{PROM}$-Bs3$_{CDS}$ construct triggered an AvrXa27-dependent HR in *Nicotiana benthamiana* leaves (FIG. 2). Importantly, AvrBs3 did not trigger HR in combination with Xa27$_{PROM}$-Bs3$_{CDS}$ (data not shown). In summary, these results indicate that the combination of AvrXa27 and the Xa27 promoter functionally replaces the combination of AvrBs3 and the Bs3 promoter.

EXAMPLE 4

Functionally Relevant Nucleotide Polymorphisms Between the Xa27 and xa27 Promoters are Located Adjacent to the Predicted TATA Box A comparison of the rice Xa27 and xa27 promoters revealed 15 polymorphisms in a genomic region of about 1000 by upstream of the transcriptional start site (Gu et al. (2005) *Nature* 435:1122-1125). It remained unclear, however, which nucleotide polymorphisms between the Xa27 and the xa27 promoters are functionally relevant. By contrast the promoters of the functionally different pepper Bs3 and Bs3-E promoters differ only in a region that is located adjacent to the TATA box. This TATA box motif in the Bs3 and Bs3-E promoters is also part of the upa$_{AvrBs3}$ box and upa$_{AvrBs3\Delta rep16}$ box. Thus, the nucleotide polymorphisms between the Xa27 and xa27 promoters that are located adjacent to the TATA box might be the functionally relevant polymorphisms and possibly part of a upa$_{AvrXa27}$ box. To test this hypothesis, the xa27 promoter was modified by site-directed mutagenesis to change the polymorphic residues adjacent to the TATA box in such a way that they are identical to corresponding residues in the Xa27 promoter sequence. Functional analysis showed that this mutated xa27 promoter was functionally identical to the Xa27 promoter (FIG. 2). Furthermore, these results provide evidence that the upa$_{AvrXa27}$ box is located in the immediate vicinity of the TATA box in the Xa27 promoter.

EXAMPLE 5

Figure 3:
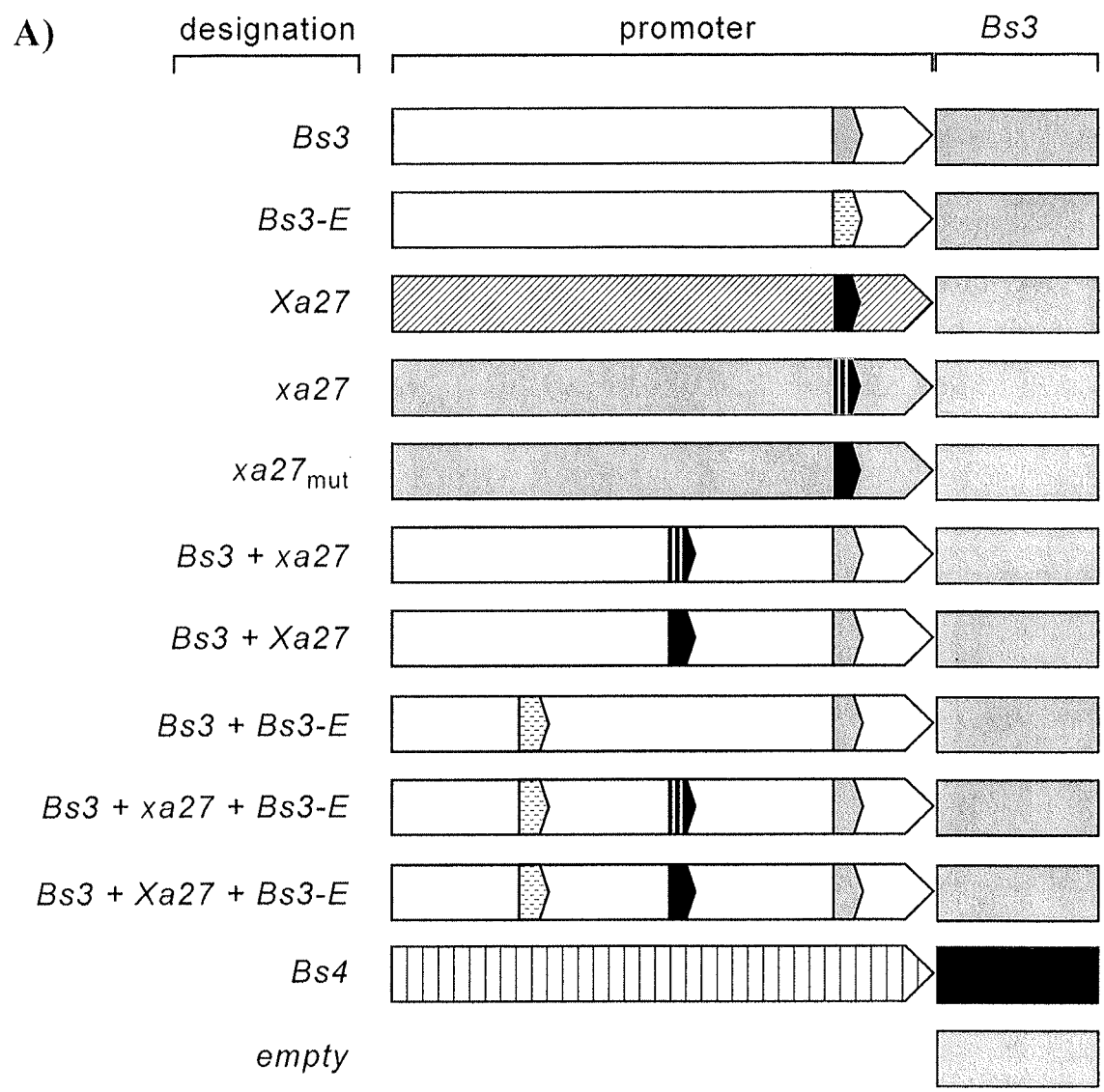
FIG. 3A. Schematic representation of the constructs that were used to study the functionality of complex promoters combining nucleotide sequence comprising the upa boxes of Bs3, Bs3-E, and Xa27 promoters. White, gray, hatched and striped boxes represent the Bs3, xa27, Xa27, and the Bs4 promoter, respectively. Small gray, dashed and black boxes represent the upa boxes from the Bs3, Bs3-E, and the Xa27 promoter. Two nucleotide polymorphisms between the upa box of the xa27 promoter (not induced by AvrXa27) and the Xa27 promoter (induced by AvrXa27) are represented by two white lines within the blue box. The xa27 and Xa27 promoter show in total 15 polymorhisms in a region of about 1 kb and are therefore displayed in different colors. The Bs3 and Bs3-E promoters differ only within their upa boxes but are otherwise identical and are therefore displayed in identical color. The black and gray rectangles represent the coding regions of the pepper Bs3 and tomato Bs4 genes.
FIG. 3B. Functional analysis of a complex promoter that combines the recognition specificity of the Bs3, Bs3-E and Xa27 promoters. The depicted promoter derivatives were delivered together with a 35S-driven avrBs3 gene (leaf on the left side), a 35-driven avrXa27 gene (leaf in the center) or a 35S-driven avrBs3Δrep16 gene (leaf on the right side) into *Nicotiana benthamiana* leaves via *Agrobacterium tumefaciens* (OD600=0.8). Dashed lines mark the inoculated areas. Four days after infiltration, the leaves were cleared to visualize the HR (dark areas). Dark areas (marked with an asterisk [*]) represent functional promoters.

The upa Boxes of the Bs3, Bs3-E and Xa27 Promoters can be Functionally Combined in One Complex Promoter The results described in Examples 1-4 resulted in the hypothesis that one can combine different upa boxes (e.g., upa$_{AvrXa27}$, upa$_{AvrBs3}$ and upa$_{AvrBs3\Delta rep16}$ boxes) into one promoter that than would be transcriptionally activated by two or more different TAL effectors. For this purpose, the upa$_{AvrXa27}$ box and the upa$_{AvrBs3\Delta rep16}$ box were introduced into the Bs3 promoter. The analysis of the different combinations of upa boxes that as depicted in FIG. 3A showed that one could functionally combine two or three upa boxes into one complex promoter (FIG. 3B). Taken together, these results demonstrate that upa boxes corresponding to different TAL effectors can be functionally combined into one complex promoter, resulting in a promoter that can be transcriptionally activated by two or more different TAL. Such a promoter finds use in the development of new strategies for increasing the resistance of a plant to multiple bacterial pathogens by introducing into the plant an R gene coding sequence that is under the control of a complex promoter as described herein.

EXAMPLE 6

Insertion of the UPT Boxes of the Rice OsTFX1, Os11N3 and Xa13 into the Pepper Bs3 Promoter The UPT$_{PthXo6}$, UPT$_{AvrXa7}$ and UPT$_{PthXo1}$ boxes (SEQ ID NOS: 31-33, respectively) of the rice OsTFX1, Os11N3 and Xa13 promoters, respectively, were each inserted separately into the pepper Bs3 promoter 5' of the upa$_{AvrBs3}$ box. The resulting promoter constructs were cloned in front of an uidA reporter gene. The Bs3 promoter-embedded UPT boxes were agro-infiltrated into *N. benthamiana* leaves in combination with the 35S promoter-driven TALe genes pthXo1, pthXo6, avrXa7 and avrBs3, respectively. GUS assays demonstrated that a Bs3 promoter derivative containing a given UPT box is transcriptionally activated only by the matching Xoo TAL effector (data not shown). For example, insertion of the UPT$_{PthXo6}$ box from the rice OsTFX1 into the pepper Bs3 promoter made this promoter construct inducible by the TAL effector PthXo6 but not PthXo1. By contrast, the Bs3 wild-type promoter (Bs3) that lacks the UPT$_{PthXo6}$ box was only inducible by AvrBs3 but not PthXo6. Similarly insertion of the UPT$_{AvrXa7}$ and UPT$_{PthXo1}$ boxes separately into the Bs3 promoter resulted in promoter constructs that were AvrXa7 and PthXo1 inducible, respectively (data not shown). All Bs3 promoter constructs contain the UPT$_{AvrBs3}$ box and thus, were also AvrBs3 inducible, irrespective of whether a Xoo UPT box was present or not (data not shown). In summary, these results demonstrate that insertion of the UPT$_{PthXo6}$, UPT$_{AvrXa7}$ and UPT$_{PthXo1}$ separately into the pepper Bs3 promoter confers upon the Bs3 promoter inducibility by the TAL effectors, PthXo6, PthXo6, and AvrXa7, respectively.

EXAMPLE 7

The Citrus UPT$_{PthAw}$ Box is Functional when Inserted into the Pepper Bs3 Promoter The production of citrus has become imperiled by the unabated spread of the bacterial disease citrus canker. The United States is the third largest citrus producer in the world, with the greatest citrus production occurring in Florida, valued at more than $9 billion (Boriss (2006) *Commodity profile: Citrus Agriculture Marketing Resource Center*, University of California; Hodges et al. (2006) *Economic impacts of the Florida citrus industry in 2003-04*, University of Florida, Institute for Food and Agriculture Sciences, EDIS document FE633). Severe economic consequences from citrus canker have occurred from the loss of marketability of fruit, reduction in fruit production and tree vigor, extra control measures, and the substantial cost incurred by eradication efforts. Various strains of *Xanthomonas* are known to cause citrus canker (Table 1). Unsuccessful attempts to eliminate the disease between 1996 and 2006 by eradication resulted in a cost of $1.2 billion and the destruction of 7 million commercial and 5 million nursery and residential trees (Bausher et al. (2006) *BMC Plant Biol.* 6:21), the largest plant-pest eradication effort ever carried out in the U.S. No new solutions have yet been deployed, and the recommended alternative management strategies are to plant windbreaks, minimize the establishment of disease with copper sprays, and control populations of leafminer, which contribute to disease spread (Graham et al. (2007) *2008 Florida citrus pest management guide for citrus canker*, University of Florida, Institute for Food and Agriculture Sciences, EDIS document PP-182). These methods do limit the extent of disease; however they are inadequate to provide effective control, and they incur additional costs, have chemical safety issues and may not be durable (Canteros (2002) Phytopathol. 92:S116). The use of other chemical control measures, such as induced systemic resistance compounds, has also been ineffective (Graham et al., 2004). The preferred control method for citrus canker, as indeed with all plant diseases, is genetic resistance, because it is generally more effective and environmentally benign. Therefore, new strategies for genetic resistance in citrus species are needed to combat the epidemic of citrus canker in Florida and other afflicted, citrus-growing regions of the world.

Toward this aim, the UPT$_{PthAw}$ box (SEQ ID NO: 41) for the TAL effector PthAw of the citrus pathogen, *Xanthomonas citri* subsp. *citri*, was inserted into the pepper Bs3 promoter 5' of the upa$_{AvrBs3}$ box. The resulting promoter construct was then cloned in front of an uidA reporter gene. This promoter construct was agro-infiltrated into *N. benthamiana* leaves in combination with the 35S promoter-driven pthAw. GUS assays demonstrated that this Bs3 promoter construct comprising a UPT$_{PthAw}$ box was transcriptionally activated when PthAw was co-expressed in the *N. benthamiana* leaves (data not shown). This result demonstrates that insertion of a citrus UPT box into the pepper Bs3 promoter confers upon the Bs3 promoter inducibility by a TAL effector from a bacterial pathogen of citrus. Such a promoter finds use in genetic resistance strategies for combating citrus canker as described hereinabove.

TABLE 1

*Xanthomonas* Strains Causing Canker on Citrus

| Strain Designation | Pathovar name(s) | Geography | Species effected |
|---|---|---|---|
| A, Asiatic | *Xanthomonas citri* subsp. *citri* Also known as: *X. campestris* pv *citri* Strain A *X. axonopodis* pv *citri* *X. smithii* subsp *citri* | Argentina, Bolivia, Brazil, China, Florida, Hong Kong, India, Japan. Malaysia, Mauritius, Pakistan, Paraguay, Philippines, Reunion Is, Rodrigues Is, Taiwan, Thailand, Uruguay, Vietnam | Wide range, high pathogenicity on sweet orange, grapefruit, Key Lime. Mandarin is more resistant. |
| Aw | Same as A | Florida | Key Lime, other citrus are immune. |
| A* | Same as A | India, Iran, Saudi Arabia | Key Lime, other citrus are immune. |
| B, Cancrosis B | *X. fuscans* subsp. *aurantifolii* | Argentina, Uruguay | Key Lime, lemons. |
| C, Cancrosis C | *X. fuscans* subsp. *aurantifolii* | Brazil | Key Lime |

EXAMPLE 8

Construction of a Complex Promoter for Genetic Resistance to Citrus Canker

A complex promoter with 14 UPT boxes from *Xanthomonas* strains that are known to cause canker on citrus was produced by inserting the 14 UPT boxes into the Bs3 promoter. To synthesize this complex promoter, restriction enzyme recognition sites for AgeI and XhoI were first introduced into the Bs3 promoter using site-directed mutagenesis. The 14 UPT boxes were inserted into this modified Bs3 promoter between the AgeI and XhoI sites. This nucleotide sequence of the complex promoter is set forth in SEQ ID NO: 34. The complex promoter retains the upa$_{AvrBs3}$ box of the wild-type Bs3 promoter and thus, is expected to be inducible by AvrBs3. The 14 UPT boxes and their TAL effectors are set forth in Table 2. This construct will be tested for inducibility by each of the 17 TAL effectors listed in Table 1. Two of the UPT boxes, UPT$_{Apl1}$ and UPT$_{PthA3}$, are expected to bind multiple TAL effectors. UPT$_{Apl1}$ is expected to bind Apl1, PthA4, and PthA-KC21. UPT$_{PthA3}$ is expected to bind PthA3 and PB3.1.

TABLE 2

UPT boxes and Citrus Canker TAL effectors

| UPT Box | TAL effector | Species | Strain | Accession number |
|---|---|---|---|---|
| UPT$_{Apl1}$ (SEQ ID NO: 35) TATAAACCTCTTTTACCTT | Apl1 | Xanthomonas citri subsp. citri | A, Asiatic | NA-1 |
| | PthA4 | Xanthomonas citri subsp. citri | A, Asiatic | 306 |
| | PthA-KC21 | Xanthomonas citri subsp. citri | A, Asiatic | KC21 |
| UPT$_{Apl2}$ (SEQ ID NO: 36) TATACACCTCTTTTACT | Apl2 | Xanthomonas citri subsp. citri | A, Asiatic | NA-1 |
| UPT$_{Apl3}$ (SEQ ID NO: 37) TACACACCTCCTACCACCTCTACTT | Apl3 | Xanthomonas citri subsp. citri | A, Asiatic | NA-1 |
| UPT$_{PthB}$ (SEQ ID NO: 38) TCTCTATCTCAACCCCTTT | PthB | X. fuscans subsp. aurantifoli | B, Cancrosis B | B69 |
| UPT$_{PthA*}$ (SEQ ID NO: 39) TATACACCTCTTTACATTT | PthA* | Xanthomonas citri subsp. citri | A* | Xc270 |
| UPT$_{PthA*2}$ (SEQ ID NO: 40) TATATACCTACACCCT | PthA*2 | Xanthomonas citri subsp. citri | A* | Xc270 |
| UPT$_{PthAw}$ (SEQ ID NO: 41) TATTTACCACTCTTACCTT | PthAw | Xanthomonas citri subsp. citri | Aw | X0053 |
| UPT$_{PthA1}$ (SEQ ID NO: 42) TATATACCTACACTACCT | PthA1 | Xanthomonas citri subsp. citri | A, Asiatic | 306 |
| UPT$_{PthA2}$ (SEQ ID NO: 43) TACACACCTCTTTTAAT | PthA2 | Xanthomonas citri subsp. citri | A, Asiatic | 306 |
| UPT$_{PthA3}$ (SEQ ID NO: 44) TACACATCTTTAAAACT | PthA3 | Xanthomonas citri subsp. citri | A, Asiatic | 306 |
| | pB3.1 | Xanthomonas citri subsp. citri | A, Asiatic | KC21 |
| UPT$_{pB3.7}$ (SEQ ID NO: 45) TATATACCTACACTACACTACCT | pB3.7 | Xanthomonas citri subsp. citri | A, Asiatic | KC21 |
| UPT$_{HssB3.0}$ (SEQ ID NO: 46) TACACATTATACCACT | HssB3.0 | Xanthomonas citri subsp. citri | A, Asiatic | KC21 |
| UPT$_{PthA}$ (SEQ ID NO: 47) TATAAATCTCTTTTACCTT | PthA | Xanthomonas citri subsp. citri | A, Asiatic | 3213 |
| UPT$_{PthC}$ (SEQ ID NO: 48) TCTCTATATAACTCCCTTT | PthC | X. fuscans subsp. aurantfoli | C, Cancrosis C | C340 |

The article "a" and "an" are used herein to refer to one or more than one (i.e., to at least one) of the grammatical object of the article. By way of example, "an element" means one or more element.

Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method for making a pathogen-inducible promoter comprising producing a nucleic acid molecule comprising a nucleotide sequence by operably linking at least two different, upa boxes, wherein the first of said at least two upa boxes is 3' of the second of said at least two upa boxes, wherein the 3' end nucleotide of said first upa box is not the 3' end nucleotide of said nucleotide sequence, and wherein said promoter is capable of inducing expression in a plant of an operably linked polynucleotide in response to at least two different TAL effectors.

2. The method of claim 1, wherein said nucleotide molecule is capable of driving pathogen-inducible expression of a polynucleotide that is operably linked to the said 3' end of said nucleotide sequence.

3. The method of claim 1, wherein at least 50, 100, 125, 150, 200, or 300 nucleotides separate said 3' end nucleotide of said first upa box and said 3' end nucleotide of said nucleotide sequence.

4. The method of claim 1, wherein said 5' end nucleotide of said second upa box is said 5' end nucleotide of said nucleotide sequence.

5. The method of claim 1, wherein said first and said second upa boxes are separated by at least at least 2, 5, 10, 25, 50, 100, 125, 150, 200, 300, 500, 750, 1000 or nucleotides.

6. The method of claim 1, wherein said first and said second upa boxes are known to bind to different TAL effectors.

7. The method of claim 1, wherein said nucleotide sequence comprises at least three upa boxes.

8. The method of claim 7, wherein the first, the second, and the third upa box of the said at least three upa boxes are each known to bind to different TAL effectors.

9. The method of claim 1, wherein at least one of said first and said second upa boxes is the upa$_{AvrBs3}$ box of SEQ ID NO: 17.

10. The method of claim 1, wherein said nucleotide sequence is selected from the group consisting of the nucleotide sequences set forth in SEQ ID NOS: 13-16 and 34.

11. A pathogen-inducible promoter produced by the method of claim 1 operably linked to a heterologous polynucleotide.

12. An expression cassette comprising a pathogen-inducible promoter produced by the method of claim 1 and an operably linked, heterologous nucleotide sequence encoding an R gene product.

13. A method for making a promoter that is inducible by two or more pathogens comprising producing a nucleic acid molecule comprising a nucleotide sequence, wherein:
   (a) said nucleotide sequence comprises at least two different, operably linked upa boxes;
   (b) the first of said at least two upa boxes is 3' of the second of said at least two upa boxes;
   (c) said 3' end nucleotide of said first upa box is not said 3' end nucleotide of said nucleotide sequence;
   (d) said first and said second upa boxes are known to bind to TAL effectors from different pathogens; and
   (e) said promoter is inducible by two or more pathogens.

14. The method of claim 13, wherein at least one of said upa boxes is the upa$_{AvrBs3}$ box of SEQ ID NO: 17.

15. The method of claim 13, wherein said nucleotide sequence is selected from the group consisting of the nucleotide sequences set forth in SEQ ID NOS: 13-16 and 34.

16. A nucleic acid molecule operably linked to a heterologous polynucleotide, wherein the nucleic acid molecule comprises a nucleotide sequence selected from the group consisting of:
   (a) the nucleotide sequences set forth in SEQ ID NO: 6, 7, 9, 13-16, or 34;
   (b) a nucleotide sequence comprising at least 95% nucleotide sequence identity to the nucleotide sequence set forth in SEQ ID NO: 6, 7, 9, 13-16, or 34, wherein said nucleotide molecule comprises upa box activity; and
   (c) a nucleotide sequence that is fully complementary to the nucleotide sequence of any one of (a)-(b).

17. An expression cassette comprising a nucleic acid molecule and a heterologous polynucleotide operably linked for expression, wherein the nucleic acid molecule comprises a nucleotide sequence selected from the group consisting of:
   (a) the nucleotide sequence set forth in SEQ ID NO: 6, 7, 9, 13-16, or 34;
   (b) a nucleotide sequence comprising at least 95% nucleotide sequence identity to the nucleotide sequence set forth in SEQ ID NO: 6, 7, 9, 13-16, or 34, wherein said nucleotide molecule comprises upa box activity; and
   (c) a nucleotide sequence that is fully complementary to the nucleotide sequence of any one of (a)-(b).

18. The expression cassette of claim 17, wherein the polynucleotide encodes an R gene product.

19. The expression cassette of claim 17, wherein said R gene product is Bs3.

20. A transformed plant comprising an expression cassette, said expression cassette comprising a nucleic acid molecule and a polynucleotide operably linked for expression, wherein the nucleic acid molecule comprises a nucleotide sequence selected from the group consisting of:
   (a) the nucleotide sequence set forth in SEQ ID NO: 6, 7, 9, 13-16, or 34;
   (b) a nucleotide sequence comprising at least 95% nucleotide sequence identity to the nucleotide sequence set forth in SEQ ID NO: 6, 7, 9, 13-16, or 34, wherein said nucleotide molecule comprises upa box activity; and
   (c) a nucleotide sequence that is fully complementary to the nucleotide sequence of any one of (a)-(b).

21. The transformed plant of claim 20, wherein said expression cassette is stably incorporated into the genome of said plant.

22. The transformed plant of claim 20, wherein said plant is a monocot or a dicot.

23. The transformed plant of claim 22, wherein said transformed plant is selected from the group consisting of pepper, tomato, tobacco, broccoli, cauliflower, cabbage, cowpea, grape, canola, bean, soybean, rice, maize, wheat, barley, citrus, cotton, cassava, walnut, eggplant, petunia, citrus spp., and *Arabidopsis*.

24. The transformed plant of claim 20, wherein said plant is a seed.

25. A non-human host cell transformed with a polynucleotide construct comprising a nucleotide sequence selected from the group consisting of:
   (a) the nucleotide sequence set forth in SEQ ID NO: 6, 7, 9, 13-16, or 34;
   (b) a nucleotide sequence comprising at least 95% nucleotide sequence identity to the nucleotide sequence set forth in SEQ ID NO: 6, 7, 9, 13-16, or 34, wherein said nucleotide molecule comprises upa box activity; and
   (c) a nucleotide sequence that is fully complementary to the nucleotide sequence of any one of (a)-(b).

26. The host cell of claim 25, wherein said nucleotide molecule further comprises an operably linked promoter or an operably linked gene of interest.

27. The host cell of claim 25, wherein said cell is selected from the group consisting of a plant cell, an animal cell, a bacterial cell, and a fungal cell.

28. The method of claim 1, wherein at least one of said first and said second upa boxes is the upa$_{AvrBs3\Delta rep16}$ box of SEQ ID NO: 18.

29. The method of claim 1, wherein at least one of said first and said second upa boxes is the upa$_{AvrXa27}$ box of SEQ ID NO: 22.

30. The method of claim 1, wherein at least one of said first and said second upa boxes is the upa$_{PthXo1}$ box of SEQ ID NO: 28 or 33.

31. The method of claim 1, wherein at least one of said first and said second upa boxes is the upa$_{PthXo6}$ box of SEQ ID NO: 29.

32. The method of claim 1, wherein at least one of said first and said second upa boxes is the upa$_{PthXo7}$ box of SEQ ID NO: 30.

33. The method of claim 1, wherein at least one of said first and said second upa boxes is the UPT$_{AvrXa7}$ box of SEQ ID NO: 32.

34. The method of claim 1, wherein at least one of said first and said second upa boxes is the UPT$_{Apl1}$ box of SEQ ID NO: 35.

35. The method of claim 1, wherein at least one of said first and said second upa boxes is UPT$_{Apl2}$ box of SEQ ID NO: 36.

36. The method of claim 1, wherein at least one of said first and said second upa boxes is the UPT$_{Apl3}$ box of SEQ ID NO: 37.

37. The method of claim 1, wherein at least one of said first and said second upa boxes is the UPT$_{PthB}$ box of SEQ ID NO: 38.

38. The method of claim 1, wherein at least one of said first and said second upa boxes is the UPT$_{PthA*}$ box of SEQ ID NO: 39.

39. The method of claim 1, wherein at least one of said first and said second upa boxes is the UPT$_{PthA*2}$ box of SEQ ID NO: 40.

40. The method of claim 1, wherein at least one of said first and said second upa boxes is UPT$_{PthAw}$ box SEQ ID NO: 41.

41. The method of claim 1, wherein at least one of said first and said second upa boxes is the UPT$_{PthA1}$ SEQ ID NO: 42.

42. The method of claim 1, wherein at least one of said first and said second upa boxes is the UPT$_{PthA2}$ box of SEQ ID NO: 43.

43. The method of claim 1, wherein at least one of said first and said second upa boxes is the UPT$_{PthA3}$ box of SEQ ID NO: 44.

44. The method of claim 1, wherein at least one of said first and said second upa boxes is UPT$_{pB3.7}$ box of SEQ ID NO: 45.

45. The method of claim 1, wherein at least one of said first and said second upa boxes is the UPT$_{HssB3.0}$ box of SEQ ID NO: 46.

46. The method of claim 1, wherein at least one of said first and said second upa boxes is the UPT$_{PthA}$ box of SEQ ID NO: 47.

47. The method of claim 1, wherein at least one of said first and said second upa boxes is the UPT$_{PthC}$ box of SEQ ID NO: 48.

48. The method of claim 13, wherein at least one of said first and said second upa boxes is the upa$_{AvrBs3\Delta rep16}$ box of SEQ ID NO: 18.

49. The method of claim 13, wherein at least one of said first and said second upa boxes is the upa$_{AvrXa27}$ box of SEQ ID NO: 22.

50. The method of claim 13, wherein at least one of said first and said second upa boxes is the upa$_{PthXo1}$ box of SEQ ID NO: 28 or 33.

51. The method of claim 13, wherein at least one of said first and said second upa boxes is the upa$_{PthXo6}$ box of SEQ ID NO: 29.

52. The method of claim 13, wherein at least one of said first and said second upa boxes is the upa$_{PthXo7}$ box of SEQ ID NO: 30.

53. The method of claim 13, wherein at least one of said first and said second upa boxes is the UPT$_{AvrXa7}$ box of SEQ ID NO: 32.

54. The method of claim 13, wherein at least one of said first and said second upa boxes is the UPT$_{Apl1}$ box of SEQ ID NO: 35.

55. The method of claim 13, wherein at least one of said first and said second upa boxes is the UPT$_{Apl2}$ box of SEQ ID NO: 36.

56. The method of claim 13, wherein at least one of said first and said second upa boxes is the UPT$_{Apl3}$ box of SEQ ID NO: 37.

57. The method of claim 13, wherein at least one of said first and said second upa boxes is the UPT$_{PthB}$ box of SEQ ID NO: 38.

58. The method of claim 13, wherein at least one of said first and said second upa boxes is the UPT$_{PthA*}$ box of SEQ ID NO: 39.

59. The method of claim 13, wherein at least one of said first and said second upa boxes is the UPT$_{PthA*2}$ box of SEQ ID NO: 40.

60. The method of claim 13, wherein at least one of said first and said second upa boxes is the UPT$_{PthAw}$ SEQ ID NO: 41.

61. The method of claim 13, wherein at least one of said first and said second upa boxes is the UPT$_{PthA1}$ box of SEQ ID NO: 42.

62. The method of claim 13, wherein at least one of said first and said second upa boxes is the UPT$_{PthA2}$ box of SEQ ID NO: 43.

63. The method of claim 13, wherein at least one of said first and said second upa boxes is the UPT$_{PthA3}$ box of SEQ ID NO: 44.

64. The method of claim 13, wherein at least one of said first and said second upa boxes is the $UPT_{pB3.7}$ box of SEQ ID NO: 45.

65. The method of claim 13, wherein at least one of said first and said second upa boxes is the $UPT_{HssB3.0}$ box of SEQ ID NO: 46.

66. The method of claim 13, wherein at least one of said first and said second upa boxes is the $UPT_{PthA}$ box of SEQ ID NO: 47.

67. The method of claim 13, wherein at least one of said first and said second upa boxes is the $UPT_{PthC}$ box of SEQ ID NO: 48.

\* \* \* \* \*